United States Patent [19]
Horiuchi et al.

[11] Patent Number: 6,046,235
[45] Date of Patent: Apr. 4, 2000

[54] SULFUR-CONTAINING AMINO ACID DERIVATIVES

[75] Inventors: Masato Horiuchi; Kenichi Fujimura; Hiroshi Suhara, all of Osaka, Japan

[73] Assignee: Santen Pharmaceutical Co., Ltd., Osaka, Japan

[21] Appl. No.: 09/254,160

[22] PCT Filed: Sep. 5, 1997

[86] PCT No.: PCT/JP97/03124

§ 371 Date: Mar. 1, 1999

§ 102(e) Date: Mar. 1, 1999

[87] PCT Pub. No.: WO98/09943

PCT Pub. Date: May 12, 1998

[30] Foreign Application Priority Data

Sep. 5, 1996 [JP] Japan .................................. 8-235145

[51] Int. Cl.⁷ ...................... A61K 31/275; C07C 255/33; C07C 309/73; C07C 229/06
[52] U.S. Cl. .......................... 514/521; 514/522; 514/523; 514/524; 514/575; 558/414; 560/13; 560/41; 562/443; 562/444; 562/449; 562/450; 562/621
[58] Field of Search ............................ 558/414; 562/621, 562/449, 443, 444; 560/13, 41; 514/522, 575, 521, 523, 524

[56] References Cited

U.S. PATENT DOCUMENTS

| | | |
|---|---|---|
| 4,749,688 | 6/1988 | Haslanger et al. . |
| 5,061,710 | 10/1991 | Haslanger et al. . |
| 5,292,926 | 3/1994 | Morita et al. . |

FOREIGN PATENT DOCUMENTS

| | | |
|---|---|---|
| 0 360 246 | 3/1990 | European Pat. Off. . |
| 61-165362 | 7/1986 | Japan . |
| 63-39855 | 2/1988 | Japan . |
| 2-776 | 1/1990 | Japan . |
| 2-134375 | 5/1990 | Japan . |
| 2-503799 | 11/1990 | Japan . |
| 8-301840 | 11/1996 | Japan . |

OTHER PUBLICATIONS

L. Klichstein et al, "Lipoxygenation of Arachidonic Acid as a Source of Polymorphonuclear Leukocyte Chemotactic Factors in Synovial Fluid and Tissue in Rheumatoid Arthritis and Spondyloarthritis", *J. Clin. Invest.*, vol. 66, pp. 1166–1170, Nov. 1980.

S.D. Brain et al, "Leukotriene $B_4$–like material in scale of psoriatic skin lesions", *Br. J. Pharmac.*, vol. 83, pp. 313–317, 1984.

P. Sharon et al, "Enhanced Synthesis of Leukotriene $B_4$ by Colonic Mucosa in Inflammatory Bowel Disease", *Gastroenterology*, vol. 86, No. 3, pp. 453–460, 1994.

S.A. Rae et al, "Leukotriene $B_4$, An Inflammatory Mediator in Gout", *The Lancet*, vol. 2, pp. 1122–1123, Nov. 20, 1982.

R. Lawrence et al, Eicosapentaenoic acid in cystic fibrosis: evidence of a pathogenetic role for leukotriene $B_4$, *The Lancet*, vol. 342, pp. 465–469, Aug. 21, 1993.

K. Koch et al, "(+)–1–(3S,4R)–[3–(4–Phenylbenzyl)–4–hydroxychroman–7–yl]cyclopentane Carboxylic Acid, a Highly Potent, Selective Leukotriene $B_4$ Antagonist with Oral Activity in the Murine Collagen–Induced Arthritis Model", *J. Med. Chem.*, vol. 37, No. 20, pp. 3197–3199, Sep. 30, 1994.

T. Komori et al, "Sulfur–Containing Acylamino Acids. I. Synthesis and Angiotensin I Converting Enzyme–Inhibitory Activities of Sulfur–Containing N–Mercaptoalkanoyl Amino Acid", *Chem. Pharm. Bull.*, vol. 35, No. 6, pp. 2382–2387, 1987.

B. Neustadt et al, "Mercaptoacyl Amino Acid Inhibitors of Atriopeptidase. 1. Structure–Activity Relationship Studies of Methionine and S–Alkylcysteine Derivatives", *J. Med. Chem.*, vol. 37, No. 15, pp. 2461–2476, 1994.

*Primary Examiner*—Johann Richter
*Assistant Examiner*—Ebenezer Sackey
*Attorney, Agent, or Firm*—Frishauf, Holtz, Goodman, Langer & Chick, P.C.

[57] ABSTRACT

A sulfur-containing amino acid compound having a high inhibitory activity on $LTA_4$ hydrolase which is represented by the following formula:

$$R^1-S-CH_2-CH(R^4)-CO-NH-CH(A^1-S-A^2-\text{Ph}-R^3)-R^2$$

wherein $R^1$ represents H, alkyl, optionally substituted phenyl alkyl, alkanoyl or optionally substituted benzoyl; $R^2$ represents ester, amide or carboxyl; $R^3$ represents hydroxyl, alkyl, halogenoalkyl, alkoxy, halogenoalkoxy, alkylthio, optionally substituted phenyl, optionally substituted phenoxy, optionally substituted phenylthio, halogen atom, alkylsulfonyl, halogenoalkylsulfonyl, nitro or cyano; $R^4$ represents alkyl; $A^1$ represents alkylene; and $A^2$ represents alkylene.

18 Claims, No Drawings

SULFUR-CONTAINING AMINO ACID DERIVATIVES

This application is a 371 of PCT/JP97/03124 filed on Sep. 5, 1997.

TECHNICAL FIELD

The present invention relates to novel sulfur-containing amino acid derivatives which have inhibitory effects on leukotriene $A_4$ hydrolase and are useful as medicines such as therapeutic agents for inflammatory diseases such as rheumatic diseases, psoriasis, inflammatory bowel diseases, gout and cystic fibrosis.

BACKGROUND ART

Leukotriene $A_4$ (hereinafter referred to as $LTA_4$) hydrolase, which is one of epoxide hydrolases, is a metal-containing enzyme which requires zinc in its active center.

$LTA_4$ hydrolase plays a catalyst-like role on biochemical conversion from $LTA_4$ into leukotriene $B_4$ (hereinafter referred to as $LTB_4$), which is a strong pro-inflammatory substance.

$LTB_4$ is an arachidonic acid metabolite which is produced in 5-lipoxygenase pathway, is biosynthesized in various cells including mast cell, neutrophil, monocyte, macrophage, etc., and plays a role as an important mediator in inflammation. $LTB_4$ induces chemotaxis, aggregation and degranulation of leukocyte and accumulation of polymorphonuclear leukocyte, and accelerates blood-vessel permeability and edema formation. For this reason, it was reported that a particularly high level of $LTB_4$ is detected at lesion sites in inflammatory diseases such as rheumatic diseases (J. Clin. Invest., 66 1166–1170 (1980)), psoriasis (Br. J. Pharmacol., 83, 313–317 (1984)), inflammatory bowel diseases (Gastroenterology, 86, 453–460 (1984)) and gout (Lancet, 2, 1122–1124 (1982)), and in sputum in cystic fibrosis (Lancet, 342, 465–469 (1993)).

Accordingly, compounds which inhibit $LTA_4$ hydrolase are expected to prevent production of $LTB_4$ and exhibit therapeutic effects on inflammatory diseases.

It was reported that 3-oxiranylbenzoic acid and derivatives thereof have inhibitory effects on $LTA_4$ hydrolase and are useful as therapeutic agents for inflammatory diseases such as psoriasis, inflammatory bowel diseases, arthritis and gout (Japanese Laid-open Patent Publication No. 134375/1990).

It was also reported that (+)-1-(3S, 4R)-[3-(4-phenylbenzyl)-4-hydroxychroman-7-yl]cyclopentanecarboxylic acid had an inhibitory effect on $LTA_4$ hydrolase and inhibited the onset of arthritis in a collagen-induced arthritis model (J. Med. Chem., 37, 3197–3199 (1994)).

On the other hand, structural features of the present compounds represented by the general formula [I] are that a sulfur atom of sulfur-containing amino acids such as cysteine is bonded to a substituted phenylalkyl group and an N-terminal is bonded to a sulfur-containing branched lower alkanoyl group. Prior art publications are described hereinafter from the standpoint of chemical structure.

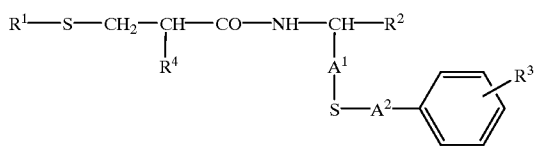

The following two kinds of known compounds have similar chemical structures to those of the present compounds; compounds of which $R^3$ is a hydrogen atom and compounds of which $R^4$ is a benzyl group in the general formula [I]. It was reported that diastereomers of the former compounds have inhibitory effects on ACE (Chem. Pharm. Bull., 35, 2382–2387 (1987)) and optically active substances of the former compounds have inhibitory effects on ACE and inhibitory effects on endopeptidase 24.11 (J. Med. Chem., 37, 2461–2476 (1994)). It was reported that the latter compounds are useful as therapeutic agents for rheumatoid diseases and antihypertensives since they have inhibitory effects on ACE and inactivating effects on rheumatoid factors (Japanese Laid-open Patent Publication No. 165362/1986), they have inhibitory effects on endopeptidase 24.11 and are useful for treatment of hypertension (Japanese Laid-open Patent Publication No. 39855/1988), and they enhance natriuretic effects of endogenous ANF and are useful for treatment of hypertension and congestive heart failure (Japanese Laid-open Patent Publication No. 503799/1990).

However, no inhibitory effect on $LTA_4$ hydrolase is described in the reports.

As mentioned above, various studies were carried out, focusing attention on the inhibitory effects on ACE, the inhibitory effects on endopeptidase 24.11, the inactivating effects on rheumatoid factors and the enhancement of natriuretic effects of endogenous ANF of the sulfur-containing amino acid derivatives. However, no study was carried out at all, focusing attention on the inhibitory effects on $LTA_4$ hydrolase about the sulfur-containing amino acid derivatives. It is a very interesting subject to study which compound has the inhibitory effect on $LTA_4$ hydrolase and how the introduction of various substituents into the compound influences the above-mentioned effect.

DISCLOSURE OF THE INVENTION

The inventors aimed at sulfur-containing amino acids such as cysteine, synthesized and studied various derivatives thereof, and measured inhibitory activities on $LTA_4$ hydrolase of the obtained compounds. As a result, the inventors found that compounds at least having the basic structure represented by the formula [II] exhibit the inhibitory activities on $LTA_4$ hydrolase.

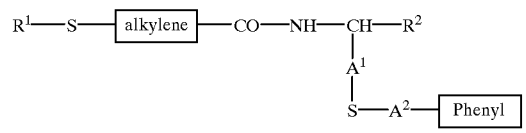

As the result of our further precise study on the compounds having excellent activities, however, it was found that it is essential in order to exhibit the excellent activities that "Phenyl" in the formula [II] is a phenyl group having a substituent and "Alkylene" in the formula [II] is an ethylene group into which a lower alkyl group is introduced. Putting these findings together, it was found that the present compounds represented by the general formula [I] have very high inhibitory activities on $LTA_4$ hydrolase. The results of the "Comparison Test" mentioned later show clearly that the above-mentioned requirements are essential for the present compounds. The present compounds are also excellent in terms of safety and are suitable compounds as medicines.

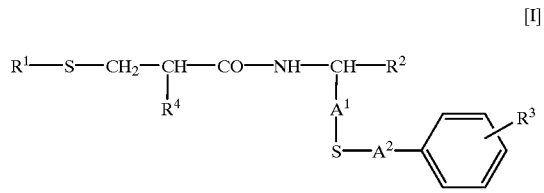

[I]

wherein $R^1$ represents a hydrogen atom, a lower alkyl group, a phenyl-lower alkyl group, a lower alkanoyl group or a benzoyl group, and each phenyl ring of the phenyl-lower alkyl group and the benzoyl group can be substituted by a lower alkyl group, a lower alkoxy group or a halogen atom.

$R^2$ represents a carboxyl group which can be converted into an ester, an amide or a hydroxamic acid.

$R^3$ represents a hydroxyl group, a lower alkyl group, a lower cycloalkyl group, a halogeno-lower alkyl group, a lower alkoxy group, a halogeno-lower alkoxy group, a lower alkylthio group, a phenyl group, a phenoxy group, a phenylthio group, a halogen atom, a lower alkylsulfonyl group, a halogeno-lower alkylsulfonyl group, a nitro group or a cyano group, and each phenyl ring of the phenyl group, the phenoxy group and the phenylthio group can be substituted by a lower alkyl group or a lower alkoxy group.

$R^4$ represents a lower alkyl group.

$A^1$ represents a lower alkylene group.

$A^2$ represents a lower alkylene group. The same definitions are applied hereinafter.

The groups defined above will be described in detail. Examples of the halogen are fluorine, chlorine, bromine and iodine. Examples of the lower alkyl are a straight or branched alkyl group having 1 to 6 carbon atoms such as methyl, ethyl, propyl, hexyl, isopropyl or tert-butyl. Examples of the lower alkanoyl are straight or branched alkanoyl having 2 to 6 carbon atoms such as acetyl, propionyl, butyryl, hexanoyl, isobutyryl or pivaloyl. Examples of the lower cycloalkyl are cyclic alkyl having 3 to 8 carbon atoms such as cyclopropane, cyclobutane, cyclopentane or cyclohexane. Examples of the lower alkoxy are straight or branched alkoxy having 1 to 6 carbon atoms such as methoxy, ethoxy, propoxy, butoxy, hexyloxy, isopropoxy or tert-butoxy. Examples of the lower alkylthio are straight or branched alkylthio having 1 to 6 carbon atoms such as methylthio, ethylthio, propylthio, butylthio, hexylthio, isopropylthio or tert-butylthio. Examples of the lower alkylene are straight or branched alkylene having 1 to 6 carbon atoms such as methylene, ethylene, trimethylene, tetramethylene, pentamethylene, hexamethylene, methylmethylene, propylene, ethylethylene, dimethylethylene, propylethylene, isopropylethylene, methyltrimethylene, dimethylmethylene, ethylmethylene, propylmethylene, isopropylmethylene or butylmethylene. Examples of the lower alkylsulfonyl are straight or branched alkylsulfonyl having 1 to 6 carbon atoms such as methylsulfonyl, ethylsulfonyl, hexylsulfonyl, isopropylsulfonyl or tert-butylsulfonyl.

The ester is a widely used ester such as an ester of carboxylic acid, exemplified by a lower alkyl ester such as methyl ester, ethyl ester, hexyl ester, isopropyl ester or tert-butyl ester, and phenyl-lower alkyl ester such as benzyl ester. The amide is awidely used amine such as an amide of carboxylic acid, exemplified by an amide with ammonia, an amide with a lower alkylamine such as methylamine, dimethylamine or ethylamine, and an amide with a phenyl-lower alkylamine such as benzylamine.

The salts of the present compound can be any pharmaceutically acceptable salt, and are not limited. Examples thereof are a salt with an inorganic acid such as hydrochloric acid, nitric acid or sulfuric acid, a salt with an alkaline metal or an alkaline earth metal such as sodium, potassium or calcium, an ammonium salt, and a salt with an organic amine such as diethylamine or triethanolamine. The present compounds can be in the form of hydrates.

By the way, in the compound used as a drug, for the purpose of promoting absorption and improving long activity in the living body and stabilizing in preparation, formation of a prodrug (e.g. esterification of a carboxylic acid) and a method of using the derivative thereof as a synthesis intermediate are used as production means. Accordingly, the carboxyl group can also be converted into the form of the ester or amide as a general purpose derivative of the carboxylic acid in the present invention.

Among the present compounds, preferred examples include the followings.

Compound (a) of the above general formula [I] wherein $R^1$ represents a hydrogen atom, a lower alkyl group, a phenyl-lower alkyl group, a lower alkanoyl group or a benzoyl group, and each phenyl ring of the phenyl-lower alkyl group and the benzoyl group can be substituted by a lower alkyl group, a lower alkoxy group or a halogen atom; $R^2$ represents a carboxyl group which can be converted into a lower alkyl ester or a phenyl-lower alkyl ester; a carboxyl group which can be converted into an amide with ammonia, a lower alkyl amine or a phenyl-lower alkyl amine; or a carboxyl group which can be converted into a hydroxamic acid, and each phenyl ring of the phenyl-lower alkyl ester and the phenyl-lower alkyl amine can be substituted by a hydroxyl group, a lower alkyl group, a lower alkoxy group, a halogen atom, a nitro group, an amino group or a lower alkylamino group; $R^3$ represents a hydroxyl group, a lower alkyl group, a lower cycloalkyl group, a halogeno-lower alkyl group, a lower alkoxy group, a halogeno-lower alkoxy group, a lower alkylthio group, a phenyl group, a phenoxy group, a phenylthio group, a halogen atom, a lower alkylsulfonyl group, a halogeno-lower alkylsulfonyl group, nitro group or a cyano group, and each phenyl ring of the phenyl group, the phenoxy group and the phenylthio group can be substituted by a lower alkyl group or a lower alkoxy group; $R^4$ represents a lower alkyl group; $A^1$ represents a lower alkylene group; and $A^2$ represents a lower alkylene group, and salts thereof.

Among those belonging to the compound (a) and salts thereof, the following compounds are exemplified as particularly preferred compounds.

A compound wherein, in the compound (a), $R^1$ represents a hydrogen atom, a lower alkanoyl group or a benzoyl group, and salts thereof.

A compound wherein, in the compound (a), $R^1$ represents a hydrogen atom or a benzoyl group, and salts thereof.

A compound wherein, in the compound (a), $R^2$ represents a carboxyl group which can be converted into a lower alkyl ester or a phenyl-lower alkyl ester; or a carboxyl group which can be converted into an amide with a lower alkyl amine or a phenyl-lower amine, and salts thereof.

A compound wherein, in the compound (a), $R^2$ represents a carboxyl group, and salts thereof.

A compound wherein, in the compound (a), $R^3$ represents a lower alkyl group, a lower cycloalkyl group, a halogeno-lower alkyl group, a lower alkoxy group, a halogeno-lower alkoxy group, a lower alkylthio group, a phenyl group, a phenoxy group, a phenylthio group, a halogen atom, a lower alkylsulfonyl group, a halogeno-lower alkylsulfonyl group, a nitro group or a cyano group, and salts thereof.

A compound wherein, in the compound (a), $R^3$ represents a lower alkyl group, a lower cycloalkyl group, a halogeno-lower alkyl group, a lower alkoxy group, a halogeno-lower alkoxy group, a lower alkylthio group, a phenyl group, a phenoxy group, a halogen atom, a lower alkylsulfonyl group, a nitro group or a cyano group, and salts thereof.

A compound wherein, in the compound (a), $R^3$ represents a methyl group, an ethyl group, a propyl group, an isopropyl group, a tert-butyl group, a cyclohexyl group, a trifluoromethyl group, a methoxy group, an ethoxy group, a trifluoromethoxy group, a methylthio group, a phenyl group, a phenoxy group, a fluorine atom, a chlorine atom, a bromine atom, an iodine atom, a methylsulfonyl group, a nitro group or a cyano group, and salts thereof.

A compound wherein, in the compound (a), $R^3$ represents a lower alkyl group, a lower cycloalkyl group, a halogeno-lower alkyl group, a lower alkylthio group or a halogen atom, and salts thereof.

A compound wherein, in the compound (a), $R^3$ represents an isopropyl group, a tert-butyl group, a cyclohexyl group, trifluoromethyl group, a methylthio group or an iodine atom, and salts thereof.

A compound wherein, in the compound (a), $R^4$ represents a methyl group, and salts thereof.

A compound wherein, in the compound (a), $A^1$ represents a methylene group or a dimethylmethylene group, and salts thereof.

A compound wherein, in the compound (a), $A^1$ represents a methylene group, and salts thereof.

A compound wherein, in the compound (a), $A^2$ represents a methylene group, a methylmethylene group, a dimethylmethylene group, an ethylmethylene group, a propylmethylene group, an isopropylmethylene group or a butylmethylene group, and salts thereof.

A compound wherein, in the compound (a), $A^2$ represents a methylene group, a methylmethylene group, a dimethylmethylene group or an ethylmethylene group, and salts thereof.

A compound wherein, in the compound (a), $A^3$ represents a lower alkyl group, a lower cycloalkyl group, a halogeno-lower alkyl group, a lower alkoxy group, a halogeno-lower alkoxy group, a lower alkylthio group, a phenyl group, a phenoxy group, a phenylthio group, a halogen atom, a lower alkylsulfonyl group, a halogeno-lower alkylsulfonyl group, a nitro group or a cyano group; and $R^4$ represents a lower alkyl group, and salts thereof.

A compound wherein, in the compound (a), $R^3$ represents a lower alkyl group, a lower cycloalkyl group, a halogeno-lower alkyl group, a lower alkoxy group, a halogeno-lower alkoxy group, a lower alkylthio group, a phenyl group, a phenoxy group, a halogen atom, a lower alkanesulfonyl group, a nitro group or a cyano group; and $R^4$ represents a lower alkyl group, and salts thereof.

A compound wherein, in the compound (a), $R^3$ represents a methyl group, an ethyl group, a propyl group, an isopropyl group, a tert-butyl group, a cyclohexyl group, a trifluoromethyl group, a methoxy group, an ethoxy group, a trifluoromethoxy group, a methylthio group, a phenyl group, a phenoxy group, a fluorine atom, a chlorine atom, a bromine atom, an iodine atom, a methylsulfonyl group, a nitro group or a cyano group; and $R^4$ represents a methyl group, and salts thereof.

A compound wherein, in the compound (a), $R^3$ represents a lower alkyl group, a lower cycloalkyl group, a halogeno-lower alkyl group, a lower alkylthio group or a halogen atom; and $R^4$ represents a lower alkyl group, and salts thereof.

A compound wherein, in the compound (a), $R^3$ represents an isopropyl group, a tert-butyl group, a cyclohexyl group, a trifluoromethyl group, a methylthio group or an iodine atom; and $R^4$ represents a methyl group, and salts thereof.

Preferred examples of the present compound include the following.

Compound (b) of the above general formula [I] wherein $R^1$ represents a hydrogen atom, a lower alkanoyl group or a benzoyl group; $R^2$ represents a carboxyl group which can be converted into a lower alkyl ester or a phenyl-lower alkyl ester; or a carboxyl group which can be converted into an amide with a lower alkyl amine or a phenyl-lower alkyl amine; $R^3$ represents a lower alkyl group, a lower cycloalkyl group, a halogeno-lower alkyl group, a lower alkoxy group, a halogeno-lower alkoxy group, a lower alkylthio group, a phenyl group, a phenoxy group, a phenylthio group, a halogen atom, a lower alkylsulfonyl group, a halogeno-lower alkylsulfonyl group, a nitro group or a cyano group; $R^4$ represents a lower alkyl group; $A^1$ represents a lower alkylene group; and $A^2$ represents a lower alkylene group, and salts thereof.

Compound (c) of the above general formula [I] wherein $R^1$ represents a hydrogen atom, a lower alkanoyl group or a benzoyl group; $R^2$ represents a carboxylic acid which can be converted into a lower alkyl ester; $R^3$ represents a lower alkyl group, a lower cycloalkyl group, a halogeno-lower alkyl group, a lower alkoxy group, a halogeno-lower alkoxy group, a lower alkylthio group, a phenyl group, a phenoxy group, a halogen atom, a lower alkylsulfonyl group, a nitro group or a cyano group; $R^4$ represents a lower alkyl group; $A^1$ represents a lower alkylene group; and $A^2$ represents a lower alkylene group, and salts thereof.

A compound wherein, in the compound (c), $R^2$ represents a carboxyl group or an ethoxycarbonyl group; $R^3$ represents a methyl group, an ethyl group, a propyl group, an isopropyl group, a tert-butyl group, a cyclohexyl group, a trifluoromethyl group, a methoxy group, an ethoxy group, a trifluoromethoxy group, a methylthio group, a phenyl group, a phenoxy group, a fluorine atom, a chlorine atom, a bromine atom, an iodine atom, a methylsulfonyl group, a nitro group or a cyano group; R⁴ represents a methyl group; A¹ represents a methylene group; and A² represents a methylene group, a methylmethylene group, a dimethylmethylene group or an ethylmethylene group, and salts thereof.

Compound (d) of the above general formula [I] wherein R¹ represents a hydrogen atom, an acetyl group or a benzoyl group; R² represents a carboxyl group, a methoxycarbonyl group or an ethoxycarbonyl group; R³ represents a methyl group, an ethyl group, a propyl group, an isopropyl group, a tert-butyl group, a trifluoromethyl group, a methoxy group, an ethoxy group, a cyclohexyl group, a trifluoromethoxy group, a methylthio group, a phenyl group, a phenoxy group, a fluorine atom, a chlorine atom, a bromine atom, an iodine atom, a methylsulfonyl group, a nitro group or a cyano group; R⁴ represents a methyl group; A¹ represents a methylene group, a methylmethylene group or a dimethylmethylene group; and A² represents a methylene group, a methylmethylene group, a dimethylmethylene group, an ethylmethylene group, a propylmethylene group, an isopropylmethylene group or a butylmethylene group, and salts thereof.

Compound (e) of the above general formula [I] wherein R¹ represents a hydrogen atom or a benzoyl group; R² represents a carboxyl group; R³ represents a lower alkyl group, a lower cycloalkyl group, a halogeno-lower alkyl group, a lower alkylthio group or a halogen atom; R⁴ represents a lower alkyl group; A¹ represents a lower alkylene group; and A² represents a lower alkylene group, and salts thereof.

A compound wherein, in the compound (e), R³ represents an isopropyl group, a tert-butyl group, acyclohexyl group, a trifluoromethyl group, a methylthio group or an iodine atom; R⁴ represents a methyl group; A¹ represents a methylene group; and A² represents a methylene group, a methylmethylene group, a dimethylmethylene group or an ethylmethyl group, and salts thereof.

Compound (f) of the above general formula [I] wherein R³ represents an isopropyl group, a tert-butyl group, a cyclohexyl group, atrifluoromethyl group, a methylthio group or an iodine atom; R⁴ represents a methyl group; A¹ represents a methylene group or a dimethylmethylene group; and A² represents methylene group, a methylmethylene group, a dimethylmethylene group or an ethylmethylene group, and salts thereof.

Preferred examples of the present compound include (2R)-2-[(2S)-3-(benzoylthio)-2-methylpropionylamino]-3-(4-isopropylbenzylthio)propionic acid [III], (2R)-2-[(2S)-3-(benzoylthio)-2-methylpropionylamino]-3-(4-tert-butylbenzylthio)propionic acid [IV], (2R)-2-[(2S)-3-(benzoylthio)-2-methylpropionylamino]-3-(4-methylthiobenzylthio)propionic acid [V], (2R)-2-[(2S)-3-(benzoylthio)-2-methylpropionylamino]-3-(4-iodobenzylthio)propionic acid [VI], (2R)-3-(4-isopropylbenzylthio)-2-[(2S)-3-mercapto-2-methylpropionylamino]propionic acid [VII], (2R)-3-(4-tert-butylbenzylthio)-2-[(2S)-3-mercapto-2-methylpropionylamino]propionic acid [VIII], (2R)-3-(4-tert-butylbenzylthio)-2-[(2RS)-3-mercapto-2-methylpropionylamino]propionic acid [IX], (2R)-2-[(2S)-3-mercapto-2-methylpropionylamino]-3-(4-methylthiobenzylthio)propionic acid [X], (2R)-3-(4-iodobenzylthio)-2-[(2S)-3-mercapto-2-methylpropionylamino]propionic acid [XI], (2R)-2-[(2S)-3-mercapto-2-methylpropionylamino]-3-[(α-methyl-4-isopropyl)benzylthio]propionic acid [XIX], (2R)-2-[(2S)-3-mercapto-2-methylpropionylamino]-3-[(α,α-dimethyl-4-isopropyl)benzylthio]propionic acid [XX], (2R)-3-[(α-ethyl-4-isopropyl)benzyithio]-2-[(2S)-3-mercapto-2-methylpropionylamino]propionic acid [XXI], (2R)-3-[(4-tert-butyl-α-methyl)benzylthio]-2-[(2R)-3-mercapto-2-methylpropionylamino]propionic acid [XXII], (2R)-3-(4-cyclohexylbenzylthio)-2-[(2S)-3-mercapto-2-methylpropionylamino]propionic acid [XXIII], (2R)-3-[(4-cyclohexyl-α,α-dimethyl)benzylthio]-2-[(2S)-3-mercapto-2-methylpropionylamino]propionic acid [XXIV], which are represented by the following formulae [III] to [XI] and [XIX] to [XXIV], and salts thereof. "Bz", "ᵗBu" and "ⁱPr" represent a benzoyl group, a tert-butyl group and an isopropyl group, respectively, in the following formulae [III] to [XI] and [XIX] to [XXIV].

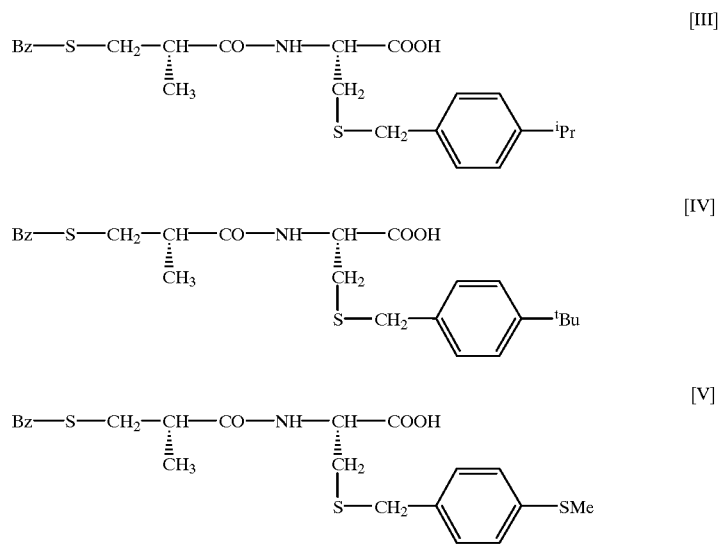

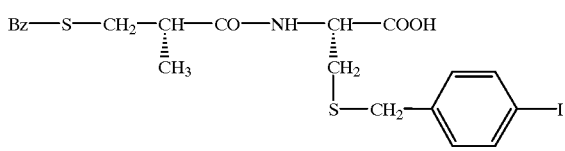
[VI]
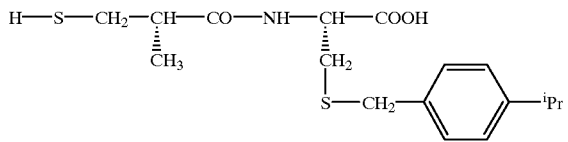
[VII]
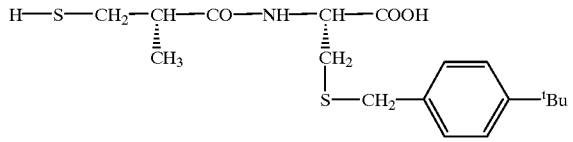
[VIII]
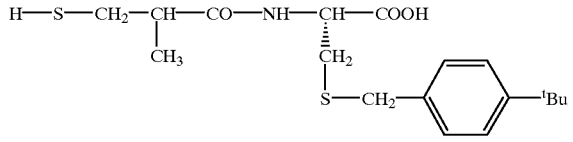
[IX]
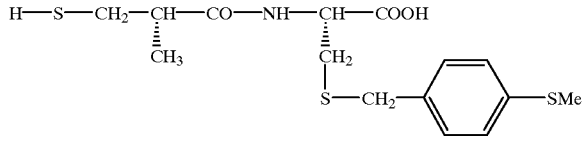
[X]
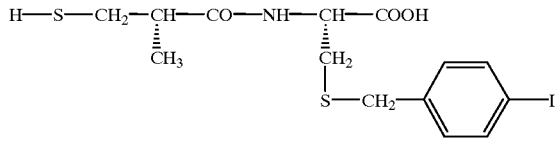
[XI]
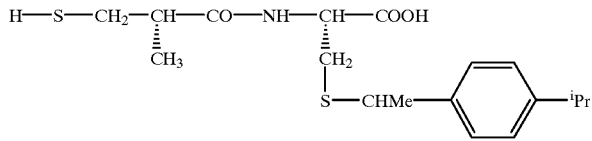
[XIX]
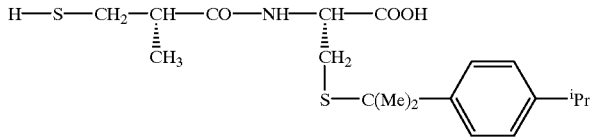
[XX]
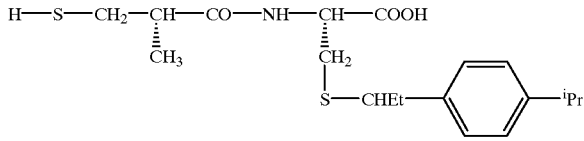
[XXI]

-continued

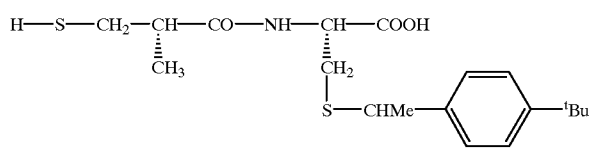
[XXII]

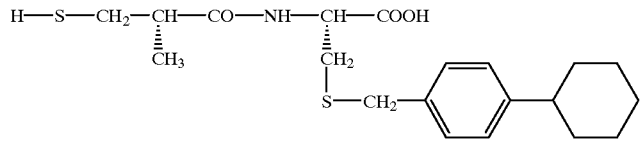
[XXIII]

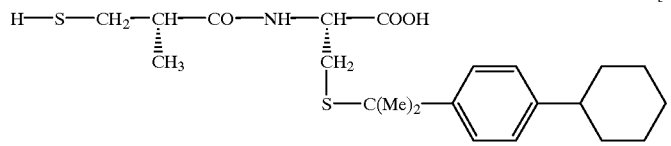
[XXIV]

The typical synthesis method of the present compound is shown hereinafter.

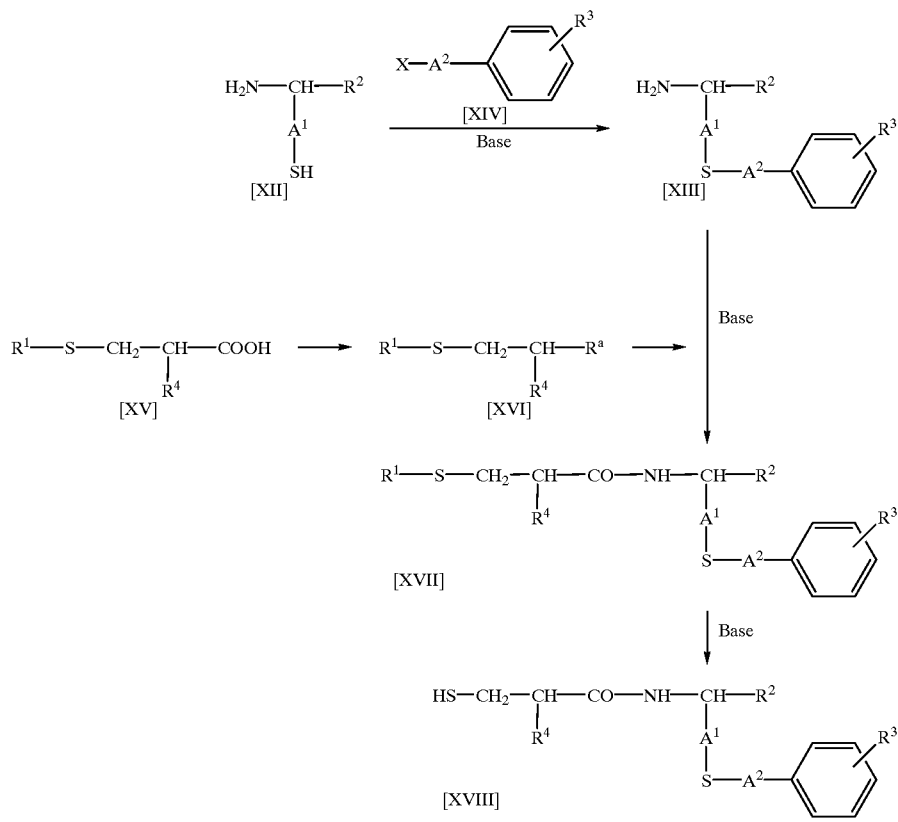

wherein $R^a$ represents an active ester of a carboxylic acid. X represents a halogen atom.

The above newly defined groups are described in more detail. The active ester is a widely used ester such as an active ester of amino acid, exemplified by 4-nitrophenyl ester or N-hydroxysuccinimide ester.

The compound represented by the above formula [XII] is allowed to react with the compound represented by the formula [XIV] in the presence of a base to give the compound represented by the formula [XIII]. Then, the compound represented by the formula [XV] is converted into the active ester represented by the formula [XVI], and the active ester is allowed to react with the compound [XIII] in the presence of a base to give the present compound (formula [XVII]) wherein $R^1$ represents a lower alkanoyl group or a benzoyl group (the phenyl ring of the benzoyl group can be substituted by a lower alkyl group, a lower alkoxy group or a halogen atom). Then, a protective group is removed, if necessary, in the presence of a base to give the present compound (formula [XVIII]) wherein $R^1$ represents a hydrogen atom.

The carboxyl group of the present compound can be converted into an ester by using a conventional method, if necessary. Furthermore, the ester can be converted into a hydroxamic acid derivative according to a conventional method. To the contrary, the ester can be converted into a carboxylic acid by hydrolysis or addition of an acid using a conventional method.

The compound obtained by the above method can be converted into the salts described above by a conventional method.

Diastereo isomers and optical isomers are present in the compound represented by the general formula, and they are included in the present invention. When using an optically active raw material, a single diastereo isomer and a single optical isomer are obtained. On the other hand, when using a racemic body as the raw material, each isomer can be separated by using a conventional method, for example, a method of using a reagent for optical resolution.

In order to examine the utility of the present compounds, studies were made on effects of the present compounds on $LTA_4$ hydrolase. The details will be shown in the pharmacological test described hereinafter. As the result of studies of the present compounds using $LTA_4$ as a substrate and measuring an amount of $LTB_4$ formed by enzymatic reaction as an indication, the present compounds exhibited high inhibitory activities on $LTA_4$ hydrolase. Accordingly, the present compounds are expected to be useful for treatment of various diseases in which $LTA_4$, which is formed by the enzymatic reaction, participates, particularly inflammatory diseases such as rheumatic diseases, psoriasis, inflammatory bowel diseases, gout and cystic fibrosis.

The present compound can be administered orally or parenterally. Examples of dosage forms are tablet, capsule, granule, powder, injection, etc. The present compound can be formulated into preparations by the conventional methods. For example, oral preparations such as a tablet, a capsule, granule and powder can be produced by adding an optionally diluent such as lactose, crystalline cellulose, starch or vegetable oil; lubricant a such as magnesium stearate or talc; a binder such as hydroxypropylcellulose or polyvinyl pyrrolidone; a disintegrator such as calcium carboxymethylcellulose or low-substituted hydroxypropylmethylcellulose; a coating agent such as hydroxypropylmethylcellulose, macrogol or silicone resin; or a gelatin film forming agent.

The dosage of the present compound can be selected suitably according to the symptom, age, dosage form and the like. In case of the oral preparation, the present compound can be administered 1 to several times per day with a daily dose of 0.1 to 5000 mg, preferably 1 to 1000 mg.

BEST MODE FOR CARRYING OUT THE INVENTION

Examples of preparations and formulations and results of pharmacological tests of the present compounds are shown below. These examples do not limit the scope of the invention, but are intended to make the invention more clearly understandable.

EXAMPLES

Preparation of Compounds

Reference Example 1

4-Nitrophenyl (2S)-3-(benzoylthio)-2-methylpropionate (reference compound No. 1-1)

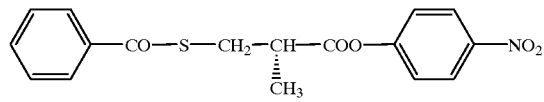

4-Nitrophenol (10.2 g) and dicyclohexylcarbodiimide (15.2 g) are added successively to a solution of (2S)-3-(benzoylthio)-2-methylpropionic acid (15 g) in methylene chloride (100 ml) under ice-cooling. The mixture is stirred under ice-cooling for 30 minutes and at room temperature for 4.5 hours. The resulting precipitate is filtered out, and the filtrate is concentrated under reduced pressure. The obtained oily residue is purified by silica gel column chromatography to give 26.01 g (quantitatively) of the titled compound. (Reference Compound No. 1-1)
mp 42.0–44.0° C.
$[\alpha]_D^{20}$ −101.2° (c=1.0, methanol)
IR (KBr, cm$^{-1}$) 3079, 2988, 1759, 1660, 1592, 1521, 1351, 1323, 1204.

The following compounds are obtained by a method similar to Reference Example 1.
4-Nitrophenyl (2R S)-3-(benzoylthio)-2-methylpropionate (reference compound No. 1-2)
mp 40.5–42.0° C.
IR (KBr, cm$^{-1}$) 3076, 2979, 1758, 1661, 1593, 1522, 1346, 1209.
4-Nitrophenyl (2RS)-3-(benzoylthio)-2-ethylpropionate (reference compound No. 1-3)
IR (film, cm$^{-1}$) 2967, 2935, 1761, 1664, 1523, 1347, 1209.
4-Nitrophenyl (2RS)-3-(benzoylthio)-2-propylpropionate (reference compound No. 1-4)
IR (film, cm$^{-1}$) 3084, 1761, 1666, 1616, 1524, 1347.
4-Nitrophenyl (2R S)-3-(benzoylthio)-2-isopropylpropionate (reference compound No. 1-5)
IR (film, cm$^{-1}$) 3083, 1758, 1665, 1616, 1524, 1347, 1315.
4-Nitrophenyl (2S)-3-(acetylthio)-2-methylpropionate (reference compound No. 1-6)
$[\alpha]_D^{20}$ −77.3° (c=0.99, methanol)
IR (film, cm$^{-1}$) 1762, 1694, 1526, 1348, 1206, 1136.

Reference Example 2

S-(4-Methylbenzyl)-L-cysteine (reference compound No. 2-1)

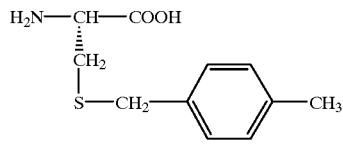

L-Cysteine hydrochloride monohydrate (2.0 g) is dissolved in a 2 N aqueous sodium hydroxide solution (11.4 ml). To the solution is added a solution of α-bromo-p-xylene (2.3 g) in ethanol (10 ml). The mixture is stirred at room temperature for 40 minutes, and precipitating crystals are filtered off. The obtained crystals are purified by recrystallization to give the titled compound.
(Reference Compound No. 2-1)
mp 210.0–211.0° C. (decomp.)
IR (KBr, cm$^{-1}$) 2919, 2115, 1618, 1581, 1495, 1421, 1298.

The following compounds are obtained by a method similar to Reference Example 2. The following compounds are obtained by the similar method by using chlorides instead of bromides as reaction substrates in reference compound Nos. 2-8, 2-9, 2-13, 2-15, 2-19, 2-20, 2-21, 2-25 and 2-26. When the halides, which are the reaction substrates, are not commercially available, the intended compounds are synthesized by using the Wohl-Ziegler method with N-bromosuccinimide from commercially available toluene compounds having substituent(s) ("Experimental Chemical Course", 4th Ed., Maruzen, Tokyo, Vol. 19, p. 428) or the chlorination method with thionyl chloride from benzyl alcohol compounds ("Experimental Chemical Course", 4th Ed., Maruzen, Tokyo, Vol. 19, p. 444).

S-(4-Methylbenzyl)-D-cysteine (reference compound No. 2-2)

S-(3-Methylbenzyl)-L-cysteine (reference compound No. 2-3)

S-(4-Ethylbenzyl)-L-cysteine (reference compound No. 2-4)
mp 195.0–197.0°C.
IR (KBr, cm$^{-1}$) 2964, 1617, 1580, 1491, 1395, 1343.

S-(4-Propylbenzyl)-L-cysteine (reference compound No. 2-5)
mp 210.0–213.0° C. (decomp.)
IR (KBr, cm$^{-1}$) 3164, 2956, 2614, 1618, 1562, 1495, 1395.

S-(4-Isopropylbenzyl)-L-cysteine (reference compound No. 2-6)
mp 200.0–205.0° C. (decomp.)
IR (KBr, cm$^{-1}$) 2959, 1585, 1491, 1412, 1342.

S-(4-tert-Butylbenzyl)-L-cysteine (reference compound No. 2-7)
mp 180.0–181.0° C. (decomp.)
IR (KBr, cm$^{-1}$) 2960, 1615, 1393, 1268, 839.

S-(4-Trifluoromethylbenzyl)-L-cysteine hydrochloride (reference compound No. 2-8)
mp 213.0–214.0° C. (decomp.)
[α]$_D^{20}$ −19.6° (c=1.0, methanol)
IR (KBr, cm$^{-1}$) 2898, 1731, 1617, 1583, 1502, 1324, 1130, 1067.

S-(4-Methoxybenzyl)-L-cysteine (reference compound No. 2-9)
mp 206.0–215.0° C. (decomp.)
IR (KBr, cm$^{-1}$) 2959, 1611, 1580, 1514, 1419, 1254.

S-(4-Ethoxybenzyl)-L-cysteine (reference compound No. 2-10)
mp 210.0–212.0° C. (decomp.)
IR (KBr, cm$^1$) 2979, 1613, 1579, 1513, 1420, 1344, 1246.

S-(4-Methylthiobenzyl)-L-cysteine (reference compound No. 2-11)
mp 210.0–213.0° C. (decomp.)
IR (KBr, cm$^{-1}$) 2918, 1617, 1579, 1492, 1419, 1343.

S-(4-Ethylthiobenzyl)-L-cysteine (reference compound No. 2-12)

S-(4-Trifluoromethoxybenzyl)-L-cysteine (reference compound No. 2-13)
mp 206.0–211.0° C. (decomp.)
IR (KBr, cm$^{-1}$) 3164, 2908, 1620, 1588, 1563, 1494, 1320.

S-(4-Phenylbenzyl)-L-cysteine (reference compound No. 2-14)

S-(4-Phenoxybenzyl)-L-cysteine (reference compound No. 2-15)
mp 208.0° C. (decomp.)
IR (KBr, cm$^{-1}$) 2915, 1579, 1490, 1420, 1258, 855, 690.

S-(4-Phenylthiobenzyl)-L-cysteine (reference compound No. 2-16)

S-(4-Fluorobenzyl)-L-cysteine (reference compound No. 2-17)
mp 210.0–215.0° C. (decomp.)
IR (KBr, cm$^{-1}$) 2915, 2617, 1621, 1583, 1558, 1491, 1411, 1394.

S-(4-Chloromethylbenzyl)-L-cysteine (reference compound No. 2-18)
mp 203.0–206.0° C. (decomp.)
IR (KBr, cm$^{-1}$) 2880, 1619, 1589, 1560, 1491, 1395, 840.

S-(4-Bromobenzyl)-L-cysteine (reference compound No. 2-19)
mp 205.0–208.0° C. (decomp.)
IR (KBr, cm$^{-1}$) 2919, 1616, 1586, 1488, 1397, 1341, 1072.

S-(4-Iodobenzyl)-L-cysteine (reference compound No. 2-20)
mp 207.0–212.0° C. (decomp.)
IR (KBr, cm$^{-1}$) 2919, 1615, 1581, 1502, 1416, 1342, 1298, 1059.

S-(4-Methylsulfonylbenzyl)-L-cysteine (reference compound No. 2-21)

S-(4-Trifluoromethylsulfonylbenzyl)-L-cysteine (reference compound No. 2-22)

S-(4-Nitrobenzyl)-L-cysteine (reference compound No. 2-23)
mp 190.0–192.0° C. (decomp.)
IR (KBr, cm$^{-1}$) 3300, 3107, 1627, 1539, 1346.

S-(4-Cyanobenzyl)-L-cysteine (reference compound No. 2-24)
mp 185.0–188.5° C. (decomp.)
IR (KBr, cm$^{-1}$) 2987, 2238, 1585, 1609, 1506.

S-(4-Isopropylbenzyl)-L-penicillamine (reference compound No. 2-25)
mp 216.5–217.9° C.
IR (KBr, cm$^{-1}$) 3128, 2960, 1637, 1509, 1462, 1378, 1329.

S-(4-Cyclohexylbenzyl)-L-cysteine (reference compound No. 2-26)
mp 195.6–197.1° C.

Reference Example 3

(2R)-2-(tert-Butoxycarbonylamino)-3-(4-methylbenzylthio)propionic acid (reference compound No. 3-1)

$$(CH_3)_3C-O-CO-NH-CH-COOH$$
$$|$$
$$CH_2$$
$$|$$
$$S-CH_2-\bigcirc-CH_3$$

Water (50 ml) and triethylamine (1.9 ml) are added to S-(4-methylbenzyl)-L-cysteine (reference compound No. 2-1) under ice-cooling. Then, a solution of di-tert-butyl dicarbonate (1.9 ml) in tetrahydrofuran (30 ml) is added thereto, and the mixture is stirred overnight at room temperature. A 10% aqueous citric acid solution is added to the system of reaction, and the whole is extracted with ethyl acetate. The organic layer is washed with water and a saturated sodium chloride solution successively, dried over anhydrous magnesium sulfate, and concentrated under reduced pressure. The obtained residue is purified by silica gel column chromatography to give the titled compound.

Reference Example 4

(2R)-2-(tert-Butoxycarbonylamino)-3-(4-methylbenzylthio)propionic acid methylamide (reference compound No. 4-1)

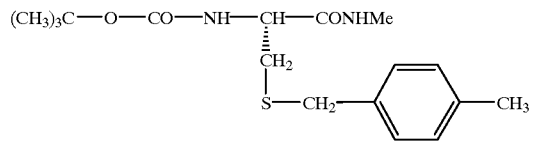

A solution of N-methylmorpholine (0.217 ml) and isobutyl chloroformate (0.256 ml) in tetrahydrofuran (5 ml) is added to a solution of (2R)-2-(tert-butoxycarbonylamino)-3-(4-methylbenzylthio)propionic acid (reference compound No. 3-1, 700 mg) in tetrahydrofuran (15 ml) under a nitrogen atmosphere and freezing medium (ice-sodium chloride) cooling, and the mixture is stirred for 15 minutes. Then, a 40% aqueous N-methylamlne solution (0.756 ml) is added thereto under a freezing medium (ice-sodium chloride) cooling, and the mixture is further stirred for two hours. A 5% aqueous sodium hydrogencarbonate solution is added to the system of reaction, and the whole is extracted with ethyl acetate. The organic layer is washed with a saturated sodium chloride solution, dried over anhydrous magnesium sulfate, and concentrated under reduced pressure. The obtained residue is purified by silica gel column chromatography to give the titled compound.

The following compound is obtained by a method similar to Reference Example 4.

(2R)-2-(tert-Butoxycarbonylamino)-3-(4-methylbenzylthio)propionic acid benzylamlde (reference compound No. 4-2)

Reference Example 5

N-tert-Butoxycarbonyl-L-cysteine ethyl ester (reference compound No. 5-1)

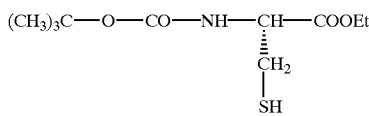

A solution of L-cysteine ethyl ester hydrochloride in methylene chloride (30 ml) is cooled with ice under a nitrogen atmosphere. To the solution are added triethylamine (4.8 ml) and a solution of di-tert-butyl dicarbonate (1.9 ml) in methylene chloride (20 ml) successively. The mixture is stirred at room temperature for 2.5 hours, and the solvent is evaporated under reduced pressure. A 5% aqueous citric acid solution is added to the residue, and the whole is extracted with ethyl acetate. The organic layer is washed with water and a saturated sodium chloride solution successively, dried over anhydrous magnesium sulfate, and concentrated under reduced pressure. The obtained residue is purified by silica gel column chromatography to give 5.41 g (93.3%) of the titled compound.

$[\alpha]_D^{20}$ −24.8° (c=1.0, methanol)

IR (film, cm$^{-1}$) 3369, 2979, 1740, 1716, 1502, 1249.

The following compound is obtained by a method similar to Reference Example 5.

N-tert-Butoxycarbonyl-L-cysteine methyl ester (reference compound No. 5-2)

Reference Example 6

S-[(α-Methyl-4-isopropyl)benzyl]-L-cysteine ethyl ester (reference compound No. 6-1)

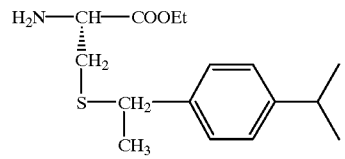

A suspension of 60% NaH (264 mg) in dimethylformamide (10 ml) is cooled with ice under a nitrogen atmosphere. To the suspension are added a solution of N-tert-butoxycarbonyl-L-cysteine ethyl ester (1.6 g) in dimethylformamide (10 ml) and a solution of (±)-1-bromo-1-(4-isopropylphenyl)ethane (1.5 g) in dimethylformamide (10 ml) successively, and the mixture is stirred at 50° to 65° C. for one hour. After allowing the mixture to stand, a 10% aqueous citric acid solution is added to the system of reaction, and the whole is extracted with ethyl acetate. The organic layer is washed with water and a saturated sodium chloride solution successively, dried over anhydrous magnesium sulfate, and concentrated under reduced pressure. A solution of 4 N hydrogen chloride/ethyl acetate (1.7 ml) is added to the residue under ice-cooling, and the mixture is stirred at room temperature for 30 minutes. Diethyl ether is added to the system of reaction, and the whole is extracted with water. A saturated aqueous sodium hydrogencarbonate solution is added to the aqueous layer so that the layer is basic, and the whole is extracted with ethyl acetate. The organic layer is washed with water and a saturated sodium chloride solution successively, dried over anhydrous magnesium sulfate, and concentrated under reduced pressure to give 127 mg (6.5%) of the titled compound.

IR (film, cm$^{-1}$) 3378, 2961, 1736, 1508, 1182, 834.

The following compound is obtained by a method similar to Reference Example 6.

S-(4-Isopropylbenzyl)-L-cysteine methyl ester (reference compound No. 6-2)

Reference Example 7

S-[(α,α-Dimethyl-4-isopropyl)benzyl]-L-cysteine hydrochloride (reference compound No. 7-1)

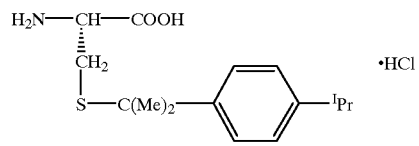

L-Cysteine hydrochloride monohydrate (3.0 g) and α,α-dimethyl-4-isopropylbenzyl alcohol (3.04 g) are mixed under a nitrogen atmosphere. The obtained mixture is dissolved in a mixed liquid of 2 N hydrochloric acid (80 ml) and dioxane (15 ml), and the mixture is stirred overnight at 55° C. After allowing to stand, triethylamine is added to the liquid so that the liquid is basic, and a solution of di-tert-butyl dicarbonate (3.74 g) in tetrahydrofuran (35 ml) is added thereto. The mixture is stirred at room temperature for 2.5 hours, and the solvent is evaporated under reduced pressure. A 5%. aqueous citric acid solution is added to the residue, and the whole is extracted with ethyl acetate. The organic layer is washed with water and a saturated sodium chloride solution successively, dried over anhydrous magnesium sulfate, and concentrated under reduced pressure. The obtained residue is purified by silica gel column chromatography, and the obtained compound is dissolved in ethyl acetate (13 ml). 4 N hydrogen chloride/ethyl acetate (13 ml) is added to the solution under ice-cooling, and the mixture is stirred at room temperature for two hours. The solvent is evaporated under reduced pressure, and the precipitated crystals are washed with diethyl ether to give 5.41 g (93.3%) of the titled compound.

mp 197.3–197.9° C.

$[\alpha]_D^{20}$ −68.0° (c=1.0, methanol)

IR (film, cm$^{-1}$) 3308, 2963, 1732, 1662, 1518, 1208, 1176, 914.

The following compounds are obtained by a method similar to Reference Example 7.

S-[(α-Ethyl-4-isopropyl)benzyl]-L-cysteine hydrochloride (reference compound No.7-2)

mp 140° C.

$[\alpha]_D^{20}$ +10.4° (c=0.51, methanol)

IR (film, cm$^{-1}$) 3405, 2961, 1925, 1574, 1508, 1220, 826.

S-[(4-tert-Butyl-α-methyl)benzyl]-L-cysteine hydrochloride (reference compound No. 7-3)

mp 200–205° C.

$[\alpha]_D^{20}$ +5.4° (c=0.51, methanol)

IR (film, cm$^{-1}$) 2963, 1744, 1483, 1224, 1192.

S-[(4-Isopropyl-α-n-propyl)benzyl]-L-cysteine hydrochloride (reference compound No. 7-4)

IR (film, cm$^1$) 2959, 1758, 1573, 1508, 1418, 1249, 1198.

S-[(4,α-Diisopropyl)benzyl]-L-cysteime hydrochloride (reference compound No. 7-5)

S-[(α-n-Butyl-4-isopropyl)benzyl]-L-cysteine hydrochloride (reference compound No. 7-6)

mp 187–189° C.

IR (film, cm$^{-1}$) 2960, 1761, 1511, 1418, 1198, 742.

S-[(4-Cyclohexyl-α,α-dimethyl)benzyl]-L-cysteine hydrochloride (reference compound No. 7-7)

mp 205.0–206.0° C.

$[\alpha]_D^{20}$ +23.9° (c=1.0, methanol)

IR (KBr, cm$^{-1}$) 2923, 1745, 1487, 1218, 1188, 844, 824.

Example 1

(2R)-2-[(2S)-3-(Benzoylthio)-2-methylpropionylamino]-3-(4-methylbenzylthio) propionic acid (compound No. 1-1)

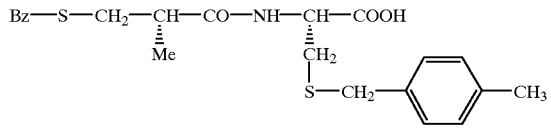

Triethylamine (0.464 ml) is added to a solution of S-(4-methylbenzyl)-L-cysteine (reference compound No. 2-1, 500 mg) in a mixed solvent of methylene chloride (20 ml)/dimethylformamide (5 ml) under ice-cooling, and the mixture is stirred. 4-Nitrophenyl (2S)-3-benzoylthio-2-methylpropionate (reference compound No. 1-1, 919 mg) is added to the system of reaction, and the system is stirred overnight. The system of reaction is further stirred overnight at 40° to 50° C. After the reaction is completed, the mixture is concentrated under reduced pressure, a 10%, aqueous citric acid solution is added to the residue, and the whole is extracted with ethyl acetate. The organic layer is washed with water and a saturated sodium chloride solution successively, dried over anhydrous sodium sulfate, and concentrated under reduced pressure. The obtained residue is purified by silica gel column chromatography to give 660 mg (68.9%) of the titled compound. (Compound No. 1-1)

mp 115.0–126.0° C.

$[\alpha]_D^{20}$ −123.8° (c=1.00, methanol)

IR (KBr, cm$^{-1}$) 3309, 2980, 1728, 1708, 1665, 1534.

The following compounds are obtained by a method similar to Example 1.

(2R)-2-[(2RS)-3-(Benzoylthio)-2-methylpropionylamino]-3-(4-methylbenzylthio) propionic acid (compound No. 1-2)

(2R)-2-[(2RS)-3-(Benzoylthio)-2-ethylpropionylamino]-3-(4-methylbenzylthio)propionic acid (compound No. 1-3)

(2R)-2-[(2RS)-3-(Benzoylthio)-2-propylpropionylamino]-3-(4-methylbenzylthio) propionic acid (compound No. 1-4)

(2R)-2-[(2RS)-3-(Benzoylthio)-2-isopropylpropionylamino]-3-(4-methylbenzylthio) propionic acid (compound No. 1-5)

(2S)-2-[(2S)-3-(Benzoylthio)-2-methylpropionylamino]-3-(4-methylbenzylthio)propionic acid (compound No. 1-6)

(2R)-2-[(2S)-3-(Benzoylthio)-2-methylpropionylamino]-3-(3-methylbenzylthio)propionic acid (compound No. 1-7)

(2R)-2-[(2S)-3-(Benzoylthio)-2-methylpropionylamino]-3-(4-ethylbenzylthio)propionic acid (compound No. 1-8)

$[\alpha]_D^{20}$ −125.2° (c=0.98, methanol)

IR (film, cm$^{-1}$) 3341, 2967, 2931, 1734, 1662, 1515, 1208.

(2R)-2-[(2S)-3-(Benzoylthio)-2-methylpropionylamino]-3-(4-propylbenzylthio)propionic acid (compound No. 1-9)

mp 119.0–121.0° C.

$[\alpha]_D^{20}$ −120.6° (c=0.51, methanol)

IR (KBr, cm$^{-1}$) 3290, 2952, 1725, 1709, 1669, 1661, 1648, 1544, 1209.

(2R)-2-[(2S)-3-(Benzoylthio)-2-methylpropionylamino]-3-(4-isopropylbenzylthio)propionic acid (compound No. 1-10)

mp 92.0–99.7° C.

$[\alpha]_D^{20}$ −123.5° (c=0.98, methanol)

IR (KBr, cm$^{-1}$) 3296, 2962, 1725, 1708, 1660, 1541, 1208.

(2R)-2-[(2S)-3-(Benzoylthio)-2-methylpropionylamino]-3-(4-tert-butylbenzylthio) propionic acid (compound No. 11-1).

$[\alpha]_D^{20}$ −89.4° (c=0.49, methanol)

IR (KBr, cm$^{-1}$) 3307, 2964, 1732, 1661, 1414, 1207, 913.

(2R)-2-[(2RS)-3-(Benzoylthio)-2-methylpropionylamino]-3-(4-tert-butylbenzylthio) propionic acid (compound No. 1-12)

IR (KBr, cm$^{-1}$) 3338, 2963, 1732, 1662, 1304, 1208, 913.

(2R)-2-[(2S)-3-(Benzoylthio)-2-methylpropionylamino]-3-(4-trifluoromethylbenzylthio)propionic acid (compound No. 1–13).

mp 180.0–180.7° C.
$[\alpha]_D^{20}$ −104.7° (c=1.0, methanol)
IR (KBr, cm$^{-1}$) 3295, 2976, 2938, 1711, 1660, 1581, 1542, 1334, 1114.

(2R)-2-[(2S)-3-(Benzoylthio)-2-methylpropionylamino]-3-(4-methoxybenzylthio)propionic acid (compound No. 1-14)

mp 133.0–138.0° C.
$[\alpha]_D^{20}$ −124.5° (c=0.97, methanol)
IR (KBr, cm$^{-1}$) 3300, 2931, 1726, 1708, 1666, 1535, 1514, 1255, 1242.

(2R)-2-[(2S)-3-(Benzoylthio)-2-methylpropionylamino]-3-(4-ethoxybenzylthio)propionic acid (compound No. 1-15)

mp 117.5–121.0° C.
$[\alpha]_D^{20}$ −123.1° (c=0.99, methanol)
IR (KBr, cm$^{-1}$) 3289, 3072, 2974, 2926, 1725, 1707, 1670, 1660, 1545, 1511, 1238, 1208.

(2R)-2-[(2S)-3-(Benzoylthio)-2-methylpropionylamino]-3-(4-methylthiobenzylthio)propionic acid (compound No. 1-16)

mp 140.8–146.0° C.
$[\alpha]_D^{20}$ −129.1° (c=0.97, methanol)
IR (KBr, cm$^{-1}$) 3292, 2975, 2920, 1724, 1707, 1668, 1660, 1650, 1542, 1208.

(2R)-2-[(2S)-3-(Benzoylthio)-2-methylpropionylamino]-3-(4-ethylthiobenzylthio)propionic acid (compound No. 1-17)

(2R)-2-[(2S)-3-(Benzoylthio)-2-methylpropionylamino]-3-(4-trifluoromethoxybenzylthio)propionic acid (compound No. 1-18)

mp 167.0–168.2° C. (decomp.)
$[\alpha]_D^{20}$ −65.6° (c=0.97, dimethyl sulfoxide)
IR (KBr, cm$^{-1}$) 3291, 2976, 1714, 1661, 1650, 1544, 1314, 1212, 1149.

(2R)-2-[(2S)-3-(Benzoylthio)-2-methylpropionylamino]-3-(4-phenylbenzylthio)propionic acid (compound No. 1-19)

(2R)-2-[(2S)-3-(Benzoylthio)-2-methylpropionylamino]-3-(4-phenoxybenzylthio)propionic acid (compound No. 1-20)

$[\alpha]_D^{20}$ −84.5° (c=0.99, methanol)
IR (KBr, cm$^{-1}$) 3285, 2933, 1659, 1591, 1240, 1207.

(2R)-2-[(2S)-3-(Benzoylthio)-2-methylpropionylamino]-3-(4-phenylthiobenzylthio)propionic acid (compound No. 1-21).

(2R)-2-[(2S)-3-(Benzoylthio)-2-methylpropionylamino]-3-(4-fluorobenzylthio)propionic acid (compound No. 1-22).

mp 146.0–150.0° C.
$[\alpha]_D^{20}$ −71.6° (c=0.99, dimethyl sulfoxide)
IR (KBr, cm$^{-1}$) 3292, 3072, 2975, 1711, 1660, 1544, 1233, 1208.

(2R)-2-[(2S)-3-(Benzoylthio)-2-methylpropionylamino]-3-(4-chlorobenzylthio)propionic acid (compound No. 1-23)

mp 162.5–165.0° C.
$[\alpha]_D^{20}$ −120.4° (c=1.0, methanol)
IR (KBr, cm$^{-1}$) 3291, 2974, 1706, 1667, 1659, 1651, 1544, 690.

(2R)-2-[(2S)-3-(Benzoylthio)-2-methylpropionylamino]-3-(4-bromobenzylthio)propionic acid (compound No. 1-24).

mp 166.0–168.3° C.
$[\alpha]_D^{20}$ −116.9° (c=1.0, methanol)
IR (KBr, cm$^{-1}$) 3292, 2976, 1708, 1659, 1542, 1285, 1242.

(2R)-2-[(2S)-3-(Benzoylthio)-2-methylpropionylamino]-3-(4-iodobenzylthio)propionic acid (compound No. 1-25)

mp 171.0–173.0° C.
$[\alpha]_D^{20}$ −76.5° (c=1.0, dimethyl sulfoxide)
IR (KBr, cm$^{-1}$) 3292, 2976, 1714, 1659, 1542, 1242, 1207.

(2R)-2-[(2S)-3-(Benzoylthio)-2-methylpropionylamino]-3-(4-methylsulfonylbenzylthio)propionic acid (compound No. 1-26)

$[\alpha]_D^{20}$ −102.2° (c=0.12, methanol)
IR (KBr, cm$^{-1}$) 3294, 2932, 1657, 1535, 1404, 1300, 1208, 1146.

(2R)-2-[(2S)-3-(Benzoylthio)-2-methylpropionylamino]-3-(4-trifluoromethylsulfonylbenzylthio)propionic acid (compound No. 1-27)

(2R)-2-[(2S)-3-(Benzoylthio)-2-methylpropionylamino]-3-(4-nitrobenzylthio)propionic acid (compound No. 1-28)

mp 169.0–171.0° C.
$[\alpha]_D^{20}$ −77.8° (c=0.97, dimethyl sulfoxide)
IR (KBr, cm$^{-1}$) 3289, 3077, 2976, 2937, 1710, 1658, 1545, 1516, 1354.

(2R)-2-[(2S)-3-(Benzoylthio)-2-methylpropionylamino]-3-(4-cyanobenzylthio)propionic acid (compound No. 1-29)

mp 155.1–156.5° C.
$[\alpha]_D^{20}$ −127.7° (c=1.0, methanol)
IR (KBr, cm$^{-1}$) 3291, 2974, 2229, 1710, 1658, 1543, 1207.

Ethyl (2R)-2-[(2S)-3-(benzoylthio)-2-methylpropionylamino]-3-[(1RS)-1-(4-isopropylphenyl)ethylthio]propionate (compound No. 1-30)

IR (film, cm$^{-1}$) 3310, 2963, 1740, 1664, 1514, 1207.

(2R)-2-[(2S)-3-(Benzoylthio)-2-methylpropionylamino]-3-(4-isopropylbenzylthio)-3-methylbutyric acid (compound No. 1-31)

$[\alpha]_D^{20}$ −82.7° (c=0.48, methanol)
IR (film, cm$^{-1}$) 3367, 2965, 1732, 1661, 1515, 1208.

Methyl (2R)-2-[(2S)-3-(benzoylthio)-2-methylpropionylamino]-3-(4-isopropylbenzylthio)propionate (compound No. 1-32)

mp 93.6–96.5° C.
$[\alpha]_D^{20}$ −121.1° (c=1.0, methanol)
IR (KBr, cm$^{-1}$) 3338, 2962, 1750, 1660, 1522, 1448, 1432, 1252, 1206, 1175, 915, 774, 688, 648.

(2R)-2-[(2S)-3-(Benzoylthio)-2-methylpropionylamino]-[(α,α-dimethyl-4-isopropyl)benzylthio]propionic acid (compound No. 1-33)

$[\alpha]_D^{20}$ −68.0° (c=1.0, methanol)
IR (film, cm$^{-1}$) 3308, 2963, 1732, 1662, 1518, 1208, 1176, 914.

(2R)-2-[(2S)-3-(Benzoylthio)-2-methylpropionylamino]-[(α-ethyl-4-isopropyl)benzylthio]propionic acid (compound No. 1-34)

$[\alpha]_D^{20}$ −90.8° (c=0.50, methanol)
IR (film, cm$^{-1}$) 2962, 2931, 1734, 1663, 1420, 1207, 1176, 914.

(2R)-2-[(2S)-3-(Benzoylthio)-2-methylpropionylamino]-3-[(4-tert-butyl-α-methyl) benzylthio]propionic acid (compound No. 1-35)

[α]$_D^{20}$ −89.5° (c=0.99, methanol)

IR (film, cm$^{-1}$) 3323, 2964, 1731, 1662, 1515, 1208, 913.

(2R)-2-[(2S)-3-(Benzoylthio)-2-methylpropionylamino]-3-(4-cyclohexylbenzylthio)propionic acid (compound No. 1-36)

[α]$_D^{20}$ −108.9° (c=0.52, methanol)

IR (film, cm$^{-1}$) 3324, 2924, 1737, 1732, 1666, 1514, 1208, 914, 757, 689.

(2R)-2-[(2S)-3-(Benzoylthio)-2-methylpropionylamino]-3-[(4-isopropyl-α-n-propyl)benzylthio]propionic acid (compound No. 1-37)

IR (film, cm$^{-1}$) 2959, 1735, 1663, 1518, 1208.

(2R)-2-[(2S)-3-(Benzoylthio)-2-methylpropionylamino]-3-[(4, α-diisopropyl)benzylthio]propionic acid (compound No. 1-38)

(2R)-2-[(2S)-3-(Benzoylthio)-2-methylpropionylamino]-3-[(α-n-butyl-4-isopropyl)benzylthio]propionic acid (compound No. (1-39)

IR (film, cm$^{-1}$) 3324, 2959, 2931, 1738, 1732, 1666, 1520, 1208, 914, 758, 689.

(2R)-2-[(2S)-3-(Benzoylthio)-2-methylpropionylamino]-3-(4-cyclohexyl-α,α-dimethylbenzylthio)propionic acid (compound No. 1-40)

[α]$_D^{20}$ −6.8° (c=1.1, methanol)

IR (film, cm$^{-1}$) 3309, 2972, 2925, 2851, 1738, 1663, 1519, 1448, 1208, 914, 756, 689.

(2R)-2-[(2S)-3-(Acetylthio)-2-methylpropionylamino]-3-(4-cyclohexylbenzylthio)propionic acid (compound No. 1-41)

mp 49.0–56.0° C. (crude crystal)

[α]$_D^{20}$ −98.7° (c=1.0, methanol)

IR (KBr, cm$^{-1}$) 3310, 2924, 1690, 1652, 1534, 1244, 1106.

(2R)-2-[(2RS)-3-(Acetylthio)-2-methylpropionylamino]-3-(4-trifluoromethylbenzylthio)propionic acid (compound No. 1-42)

Example 2

(2R)-2-[(2S)-3-Mercapto-2-methylproplonylamino]-3-(4-methylbenzylthio)propionic acid (compound No. 2-1)

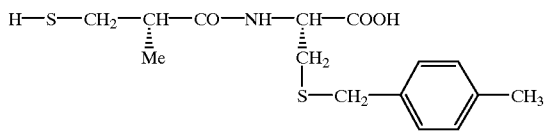

A 28% aqueous ammonia solution (6 ml) is added to (2R)-2-[(2S)-3-(benzoylthio)-2-methylpropionylamino]-3-(4-methylbenzylthio)propionic acid (compound No. 1-1, 200 mg) under a nitrogen atmosphere, and the mixture is stirred at room temperature for one hour. Ethyl acetate is added to the system of reaction, and the whole is extracted with water. 6 N hydrochloric acid is added to the aqueous layer under ice-cooling to adjust pH to 2, and the whole is extracted with ethyl acetate. The organic layer is washed with water and a saturated sodium chloride solution successively, dried over anhydrous magnesium sulfate, and concentrated under reduced pressure. The obtained residue is purified by silica gel column chromatography to give 94 mg (62.3%) of the titled compound.

mp 86.0–88.5° C.

[α]$_D^{20}$ −71.6° (c=0.51, methanol)

IR (KBr, cm$^{-1}$) 3458, 3292, 2975, 2935, 1744, 1723, 1643, 1542.

The following compounds are obtained by a method similar to Example 2.

(2R)-2-[(2RS)-3-Mercapto-2-methylpropionylamino]-3-(4-methylbenzylthio)propionic acid (compound No. 2-2)

(2R)-2-[(2RS)-2-Ethyl-3-mercaptopropionylamino]-3-(4-methylbenzylthio)propionic acid (compound No. 2-3)

(2R)-2-[(2RS)-3-Mercapto-2-propylpropionylamino]-3-(4-methylbenzylthio)propionic acid (compound No. 2-4)

(2R)-2-[(2S)-3-Mercapto-2-isopropylpropionylamino]-3-(4-methylbenzylthio) propionic acid (compound No. 2-5)

(2S)-2-[(2S)-3-Mercapto-2-methylpropionylamino]-3-(4-methylbenzylthio)propionic acid (compound No. 2-6)

(2R)-2-[(2S)-3-Mercapto-2-methylpropionylamino]-3-(3-methylbenzylthio)propionic acid (compound No. 2-7)

(2R)-3-(4-Ethylbenzylthio)-2-[(2S)-3-mercapto-2-methylpropionylamino]propionic acid (compound No. 2-8)

mp 49.5–52.5° C.

[α]$_D^{20}$ −67.5° (c=0.99, methanol)

IR (KBr, cm$^{-1}$) 3321, 2964, 2517, 1714, 1643, 1540, 1418, 1198.

(2R)-2-[(2S)-3-Mercapto-2-methylpropionylamino]-3-(4-propylbenzylthio)propionic acid (compound No. 2-9)

mp 87.0–89.50° C.

[α]$_D^{20}$ −70.1° (c=0.51, methanol)

IR (KBr, cm$^{-1}$) 3332, 2958, 2930, 1744, 1723, 1644, 1603, 1542, 1416, 1220, 1196.

(2R)-3-(4-Isopropylbenzylthio)-2-[(2S)-3-mercapto-2-methylpropionylamino]propionic acid (compound No. 2-10)

[α]$_D^{20}$ −61.1° (c=0.52, methanol)

IR (film, cm$^{-1}$) 3324, 2961, 2567, 1729, 1648, 1515, 1213.

(2R)-3-(4-tert-Butylbenzylthio)-2-[(2S)-3-mercapto-2-methylpropionylamino]propionic acid (compound No. 2-11)

[α]$_D^{20}$ −52.0° (c=0.49, methanol)

IR (film, cm$^{-1}$) 3376, 2965, 1725, 1643, 1515, 1216.

(2R)-3-(4-tert-Butylbenzylthio)-2-[(2RS)-3-mercapto-2-5 methylpropionylamino]propionic acid (compound No. 2-12)

IR (film, cm$^{-1}$) 3308, 2567, 1731, 1517, 1203.

(2R)-2-[(2S)-3-Mercapto-2-methylpropionylamino]-3-(4-trifluoromethylbenzylthio)propionic acid (compound No. 2-13)

mp 82.0–84.2° C.

[α]$_D^{20}$ −66.2° (c=0.48, methanol)

IR (KBr, cm$^{-1}$) 3314, 2567, 1734, 1654, 1524, 1322, 1170, 1123.

(2R)-2-[(2S)-3-Mercapto-2-methylpropionylamino]-3-(4-methoxybenzylthio)propionic acid (compound No. 2-14)

mp 87.0–93.0° C.

[α]$_D^{20}$ −73.5° (c=1.0, methanol)

IR (KBr, cm$^{-1}$) 3294, 2971, 2935, 1722, 1708, 1648, 1540, 1513, 1248.

(2R)-3-(4-Ethoxybenzylthio)-2-[(2S)-3-mercapto-2-methylpropionylamino]propionic acid (compound No. 2-15)

mp 85.0–87.0° C.
[α]$_D$$^{20}$ −68.3° (c=0.51, methanol)
IR (KBr, cm$^{-1}$) 3330, 2979, 2934, 2511, 1718, 1697, 1645, 1607, 1542, 1512, 1250.

(2R)-2-[(2S)-3-Mercapto-2-methylpropionylamino]-3-(4-methylthiobenzylthio)propionic acid (compound No. 2-16)

mp 87.0–92.0° C.
[α]$_D$$^{20}$ −75.2° (c=0.55, methanol)
IR (KBr, cm$^{-1}$) 3285, 2967, 2928, 2544, 1723, 1706, 1650, 1537, 1420, 1281, 1255.

(2R)-3-(4-Ethylthiobenzylthio)-2-[(2S)-3-mercapto-2-methylpropionylamino]propionic acid (compound No. 2-17)

(2R)-2-[(2S)-3-Mercapto-2-methylpropionylamino]-3-(4-trifluoromethoxybenzylthio)propionic acid (compound No. 2-18)

mp 55.0–62.0° C.
[α]$_D$$^{20}$ −58.6° (c=0.97, methanol)
IR (KBr, cm$^{-1}$) 3331, 2974, 2937, 1725, 1647, 1605, 1542, 1509, 1288.

(2R)-2-[(2S)-3-Mercapto-2-methylpropionylamino]-3-(4-phenylbenzylmethylthio)propionic acid (compound No. 2-19)

mp 92.0–101.0° C.
[α]$_D$$^{20}$ −66.2° (c=0.11, methanol)
IR (KBr, cm$^{-1}$) 3304, 2931, 1703, 1647, 1530, 1408, 1276, 1250.

(2R)-2-[(2S)-3-Mercapto-2-methylpropionylamino]-3-(4-phenoxybenzylthio)propionic acid (compound No. 2-20)

[α]$_D$$^{20}$ −58.4° (c=0.5, methanol)
IR (film, cm$^{-1}$) 2932, 2568, 1733, 1589, 1236.

(2R)-2-[(2S)-3-Mercapto-2-methylpropionylamino]-3-(4-phenylthiobenzylthio)propionic acid (compound No. 2-21)

(2R)-3-(4-Fluorobenzylthio)-2-[(2S)-3-mercapto-2-methylpropionylamino]propionic acid (compound No. 2-22)

mp 66.5–73.0° C.
[α]$_D$$^{20}$ −72.5° (c=1.0, methanol)
IR (KBr, cm$^{-1}$) 3334, 3282, 2972, 2360, 1742, 1716, 1643, 1599, 1544, 1509, 1219.

(2R)-3-(4-Chlorobenzylthio)-2-[(2S)-3-mercapto-2-methylpropionylamino]propionic acid (compound No. 2-23)

mp 79.0–92.0° C.
[α]$_D$$^{20}$ −69.7° (c=0.48, methanol)
IR (KBr, cm$^{-1}$) 3283, 2542, 1716, 1643, 1542, 1418.

(2R)-3-(4-Bromobenzylthio)-2-[(2S)-3-mercapto-2-methylpropionylamino]propionic acid (compound No. 2-24)

mp 85.0–94.0° C.
[α]$_D$$^{20}$ −63.1° (c=0.53, methanol)
IR (KBr, cm$^{-1}$) 3286, 2972, 2934, 1741, 1723, 1703, 1644, 1603, 1542, 1069.

(2R)-3-(4-Iodobenzylthio)-2-[(2S)-3-mercapto-2-methylpropionylamino]propionic acid (compound No. 2-25)

mp 109.5–111.5° C.
[α]$_D$$^{20}$ −60.6° (c=0.52, methanol)
IR (KBr, cm$^{-1}$) 3331, 3288, 2972, 2934, 1722, 1644, 1604, 1541, 1414, 1393, 1182, 1058.

(2R)-2-[(2S)-3-Mercapto-2-methylpropionylamino]-3-(4-methylsulfonylbenzylthio)propionic acid (compound No. 2-26)

mp 121.5–126.5° C.
[α]$_D$$^{20}$ −61.8° (c=0.099, methanol)
IR (KBr, cm$^{-1}$) 3319, 2970, 2575, 1708, 1643, 1537, 1293, 1233, 1131.

(2R)-2-[(2S)-3-Mercapto-2-methylpropionylamino]-3-(4-trifluoromethylsulfonylbenzylthio)propionic acid (compound No. 2-27)

(2R)-2-[(2S)-3-Mercapto-2-methylpropionylamino]-3-(4-nitrobenzylthio)propionic acid (compound No. 2-28)

[α]$_D$$^{20}$ −53.0° (c=0.49, dimethyl sulfoxide)
IR (KBr, cm$^{-1}$) 3306, 2932, 2569, 1731, 1632, 1519, 1422, 1346.

(2R)-3-(4-Cyanobenzylthio)-2-[(2S)-3-mercapto-2-methylpropionylamino]propionic acid (compound No. 2-29)

[α]$_D$$^{20}$ −66.3° (c=0.59, methanol)
IR (film, cm$^{-1}$) 3340, 2972, 2932, 2568, 2229, 1733, 1650, 1533, 1214.

(2R)-2-[(2S)-3-Mercapto-2-methylpropionylamino]-3-[(α-methyl-4-isopropyl)benzylthio]propionic acid (compound No. 2-30)

IR (film, cm$^{-1}$) 3310, 2963, 1740, 1664, 1514, 1207.

(2R)-2-[(2S)-3-Mercapto-2-methylpropionylamino]-3-methyl-3-(4-isopropylbenzylthio)butyric acid (compound No. 2-31)

[α]$_D$$^{20}$ −23.1° (c=0.20, methanol)
IR (film, cm$^1$) 3361, 2964, 2568, 1727, 1648, 1515, 1217.

(2R)-2-[(2S)-3-Mercapto-2-methylpropionylamino]-3-[(α,α-dimethyl-4-isopropyl)benzylthio]propionic acid (compound No. 2-32)

[α]$_D$$^{20}$ −24.7° (c=0.51, methanol)
IR (film, cm$^{-1}$) 3318, 2962, 2568, 1731, 1646, 1518, 1383, 1195.

(2R)-3-[(α-Ethyl-4-isopropyl)benzylthio]-2-[(2S)-3-mercapto-2-methylpropionylamino]propionic acid (compound No. 2-33)

[α]$_D$$^{20}$ −43.5° (c=0.48, methanol)
IR (film, cm$^{-1}$) 3310, 2962, 2564, 1731, 1646, 1522, 1420, 1208.

(2R)-3-[(4-tert-Butyl-α-methyl)benzylthio]-2-[(2R)-3-mercapto-2-methylpropionylamino]propionic acid (compound No. 2-34)

IR (KBr, cm$^{-1}$) 2965, 2565, 1732, 1650, 1519, 1218.

(2R)-3-(4-Cyclohexylbenzylthio)-2-[(2S)-3-mercapto-2-methylpropionylamino]propionic acid (compound No. 2-35)

mp 106.6–109.0° C.
[α]$_D$$^{20}$ −65.2° (c=0.36, methanol)
IR (KBr, cm$^{-1}$) 3318, 2923, 1716, 1655, 1525, 1426, 1266.

(2R)-2-[(2S)-3-Mercapto-2-methylpropionylamino]-3-[(4-isopropyl-α-n-propyl)benzylthio]propionic acid (compound No. 2-36)

IR (film, cm$^{-1}$) 2959, 2570, 1732, 1644, 1522, 1216.

(2R)-2-[(2S)-3-Mercapto-2-methylpropionylamino]-3-[(4, α-diisopropyl)benzylthio]propionic acid (compound No. 2-37)

IR (film, cm$^{-1}$) 3318, 2960, 2571, 1732, 1644, 1524, 1215.

(2R)-3-[(α-n-Butyl-4-isopropyl)benzylthio]-2-[(2S)-3-mercapto-2-methylpropionylamino]propionic acid (compound No. 2-38)

IR (film, cm$^{-1}$) 3314, 2959, 1732, 1642, 1521, 1194, 840, 761, 572.

(2R)-3-[(4-Cyclohexyl-α,α-dimethyl)benzylthio]-2-[(2S)-3-mercapto-2-methylpropionylamino]propionic acid (compound No. 2-39)

$[\alpha]_D^{20}$ −56.2° (c=1.0, methanol)

IR (film, cm$^{-1}$) 2924, 1740, 1641, 1610, 1444, 1197.

Example 3

(2R)-2-[(2S)-3-(Benzoylthio)-2-methylpropionylamino]-3-(4-methylbenzylthio) propionic acid methylamide (compound No. 3-1)

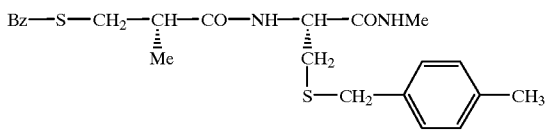

4 N hydrogen chloride/dioxane (1.5 ml) is added to (2R)-2-(tert-butoxycarbonylamino)-3-(4-methylbenzylthio) propionic acid methylamide (reference compound No. 4-1, 200 mg), and the mixture is stirred at room temperature for one hour. The reaction mixture is concentrated under reduced pressure, and the obtained residue is dissolved in methylene chloride (5 ml). To the solution are added N-methylmorpholine (0.119 ml), 1-hydroxybenzotriazole (109 mg), (2S)-3-(benzoylthio)-2-methylpropionic acid (182 mg), 1-ethyl-3-(3-dimethylaminopropyl)carbodiimide hydrochloride (135 mg) and N-methylmorpholine (0.077 ml) successively under ice-cooling, and the mixture is stirred overnight at room temperature. A 5% aqueous sodium hydrogencarbonate solution is added to the system of reaction, and the whole is extracted with ethyl acetate. The organic layer is washed with a 5% aqueous sodium hydrogencarbonate solution and a saturated sodium chloride solution successively, dried over magnesium sulfate, and concentrated under reduced pressure. The obtained residue is purified by silica gel column chromatography to give the titled compound.

The following compound is obtained by a method similar to Example 3.

(2R)-2-[(2S)-3-(Benzoylthio)-2-methylpropionylamino]-3-(4-methylbenzylthio)propionic acid benzylamide (compound No. 3-2)

Example 4

(2R)-2-[(2S).-3-Mercapto-2-methylproplonylamino]-3-(4-methylbenzylthio)propionic acid methylamide (compound No. 4-1)

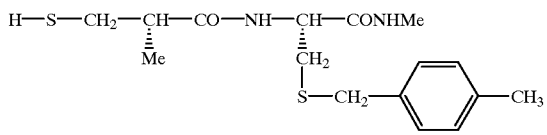

A 1 N aqueous sodium hydroxide solution (0.13 ml) is added to a solution of (2R)-2-[(2S)-3-(benzoylthio)-2-methylpropionylamino]-3-(4-methylbenzylthio)propionic acid methylamide (compound No. 3-1, 50 mg) in methanol (2 ml), and the mixture is stirred at room temperature for 15 minutes. A 5% aqueous citric acid solution is added to the system of reaction to adjust pH to 7, and the mixture is concentrated under reduced pressure. Water is added to the obtained residue, and the whole is extracted with ethyl acetate. The organic layer is washed with a saturated sodium chloride solution, dried over anhydrous magnesium sulfate, and concentrated under reduced pressure to give the titled compound.

The following compound is obtained by a method similar to Example 4.

(2R)-2-[(2S)-3-Mercapto-2-methylpropionylamino]-3-(4-methylbenzylthio)proplonic acid benzylamide (compound No. 4-2)

Example 5

Methyl (2R)-2-[(2S)-3-mercapto-2-methylpropionylamino]-3-(4-methylbenzylthio) propionate (compound No. 5-1)

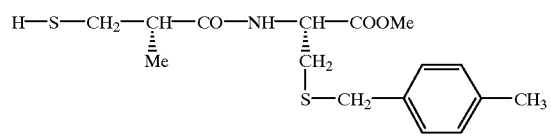

Anhydrous sodium sulfate (3 g) is added to a solution of (2R)-2-[(2S)-3-mercapto-2-methylpropionylamino]-3-(4-methylbenzylthio)propionic acid (compound No. 1-1, 300 mg) and p-toluenesulfonic acid monohydrate (240 mg) in methanol (10 ml), and the mixture is refluxed for three hours and 30 minutes. Sodium sulfate is filtered out, and the filtrate is concentrated under reduced pressure. A 5% aqueous sodium hydrogencarbonate solution is added to the obtained residue, and the whole is extracted with ethyl acetate. The organic layer is washed with a 5% aqueous sodium hydrogencarbonate solution, a 5% aqueous citric acid solution and a saturated sodium chloride solution successively, dried over anhydrous sodium sulfate, and concentrated under reduced pressure to give the titled compound. The following compound is obtained by a method similar to Example 5.

Benzyl (2R)-2-[(2S)-3-mercapto-2-methylpropionylamino]-3-(4-methylbenzylthio) proplonate (compound No. 5-2)

Example 6

(2R)-3-[(1RS)-1-(4-Isopropylphenyl)ethylthio]-2-[(2S)-3-mercapto-2-methylproplonylamino] propionic acid (compound No. 6-1)

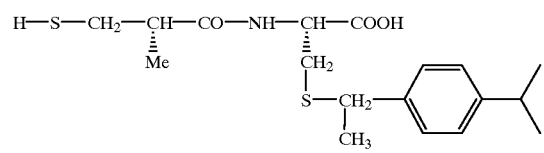

A solution of ethyl (2R)-2-[(2S)-3-(benzoylthio)-2-methylpropionylamino]-3-[(1RS)-1-(4-isopropylphenyl) ethylthio]propionate (190 mg) in a mixed solvent of methanol (2 ml)/tetrahydrofuran (0.5 ml) is cooled with ice under a nitrogen atmosphere. A 2 N aqueous lithium hydroxide solution (420 ml) is added thereto, the temperature is raised to room temperature, and the mixture is stirred for 45 minutes. Ethyl acetate is added to the system of reaction, and the whole is extracted with water. A 10% aqueous citric acid solution is added to the aqueous layer to adjust pH to 3, the whole is extracted with ethyl acetate, and the organic layer is washed with water and a saturated sodium chloride solution successively. The organic layer is dried over anhydrous magnesium sulfate, and concentrated under reduced pressure. The obtained residue is purified by silica gel column chromatography to give 57 mg (40.7%) of the titled compound.

IR (film, cm$^{-1}$) 3307, 2962, 2567, 1732, 1637, 1522, 1217.

Formulation

General formulation examples of oral preparations and injections using the present compounds are shown below.

| 1) Tablet Formulation 1 in 100 mg | |
|---|---|
| Present compound | 1 mg |
| Lactose | 66.4 mg |
| Corn starch | 20 mg |
| Calcium carboxymethylcellulose | 6 mg |
| Hydroxypropylcellulose | 4 mg |
| Magnesium stearate | 0.6 mg |

Tablets according to the formulation as above are coated with 2 mg/tablet of a coating agent (this is an ordinary coating agent such as hydroxypropylcellulose, macrogol or silicone resin) to obtain desired coating tablets. (The same is applied to tablets mentioned below.)

| Formulation 2 in 100 mg | |
|---|---|
| Present compound | 5 mg |
| Lactose | 62.4 mg |
| Corn starch | 20 mg |
| Calcium carboxymethylcellulose | 6 mg |
| Hydroxypropylcellulose | 4 mg |
| Magnesium stearate | 0.6 mg |
| Coating agent | 2 mg |
| Formulation 3 in 100 mg | |
| Present compound | 20 mg |
| Lactose | 51 mg |
| Corn starch | 15 mg |
| Calcium carboxymethylcellulose | 5 mg |
| Hydroxypropylcellulose | 5 mg |
| Magnesium stearate | 1 mg |
| Talc | 1 mg |
| Coating agent | 2 mg |
| Formulation 4 in 100 mg | |
| Present compound | 40 mg |
| Lactose | 34 mg |
| Corn starch | 10 mg |
| Calcium carboxymethylcellulose | 5 mg |
| Hydroxypropylcellulose | 5 mg |
| Magnesium stearate | 2 mg |
| Talc | 2 mg |
| Coating agent | 2 mg |
| Formulation 5 in 220 mg | |
| Present compound | 100 mg |
| Lactose | 67 mg |
| Corn starch | 20 mg |
| Calcium carboxymethylcellulose | 10 mg |
| Hydroxypropylcellulose | 10 mg |
| Magnesium stearate | 4 mg |
| Talc | 4 mg |
| Coating agent | 5 mg |
| 2) Capsule Formulation 1 in 150 mg | |
| Present compound | 5 mg |
| Lactose | 145 mg |

Varying the mixing ratio of the present compound to lactose, capsules having the contents of the present compound of 10 mg/capsule, 30 mg/capsule, 50 mg/capsule and 100 mg/capsule are also prepared.

| 3) Granule Formulation 1 in 100 mg | |
|---|---|
| Present compound | 30 mg |
| Mannitol | 46.5 mg |
| Polyvinyl pyrrolidone K-30 | 7 mg |
| Eudragit RL | 15 mg |
| Triacetin | 1.5 mg |
| Formulation 2 in 130 mg | |
| Present compound | 50 mg |
| Lactose | 55 mg |
| White potato starch | 20 mg |
| Hydroxypropylcellulose | 4 mg |
| Talc | trace |
| 4) Injection Formulation 1 in 10 ml | |
| Present compound | 10–100 mg |
| Sodium chloride | 90 mg |
| Sodium hydroxide | q.s. |
| Sterile purified water | q.s. |

Pharmacological Test

Izumi et al. had reported a method of measuring LTA$_4$ hydrolase activity by measuring an amount of LTB$_4$ produced by an enzymatic reaction using LTA$_4$ as a substrate (Biochem. Biophys. Res. Commun., 135, 139–145 (1986)). Effects of the present compounds on LTA$_4$ hydrolase were examined according to the method described in the literature.

Experimental Method

An enzyme preparation used in this pharmacological test was prepared by extracting roughly from guinea pig lung by the following method, according to the method of Izumi et al. (Biochem. Biophys. Res. Commun., 135, 139–145 (1986)) and the method of Evans et al. (Biochem. Biophys. Acta, 840, 43–50 (1985)).

Lungs were excised from a Hartley guinea pig (body weight: 330 g). The lungs were homogenized in phosphoric acid buffer (50 mM, pH 7.4, containing 1 mM ethylenediaminetetraacetic acid (EDTA) and 1 mM dithiothreitol (DTT) having weight three times that of the lungs under ice-cooling. The homogenate was centrifuged at low speed (800×g) for 20 minutes, centrifuged at high speed (10,000× g) for 20 minutes and ultracentrifuged (100,000×g) for 60 minutes to give a supernatant. The supernatant was brought to 40% saturation by adding a saturated aqueous ammonium sulfate solution (pH 7.0–7.2, containing 1 mM DTT) dropwise under ice-cooling and centrifuged at high speed (10,000×g) for 20 minutes. The resulting supernatant was brought to 70% saturation by adding a saturated aqueous ammonium sulfate solution (pH 7.0–7.2, containing 1 mM DTT) dropwise and centrifuged at high speed (10,000×g) for 20 minutes. The obtained pellet was dissolved in 2 ml of Tris-acetic acid buffer (20 mM, pH 7.8, containing 1 mM DTT) and dialyzed in 2 liters of the solution to give the enzyme preparation.

LTA$_4$ used, which is the substrate, was prepared by hydrolyzing LTA$_4$ methyl ester and dissolved in ethanol.

In order to examine effects of the present compounds on the enzyme preparation, reactions were performed under the following condition using mixed solutions consisting of the composition shown in Table 1.

TABLE 1

| | |
|---|---|
| HEPES buffer | 50 mM, pH 7.8 |
| Enzyme preparation | 0.4–0.6 mg protein |
| $LTA_4$ | 63 μM |
| Aqueous DTT solution | 3 mM |
| Test compound | $10^{-8}$–$10^{-3}$ M |

The above-mentioned solution (50 μl) was incubated at 37° C. for one minute. To the reaction mixture was added 100 μl of a mixed liquid of acetonitrile-ethanol-acetic acid (150:50:3, volume ratio) under ice-cooling. The mixture was allowed to stand at −20° C. for 30 minutes and centrifuged at high speed (10,000×g) for five minutes to give a supernatant. An amount of $LTB_4$ produced in the supernatant was measured by high-speed liquid chromatography.

The degree of the inhibitory effect of each test compound on $LTA_4$ hydrolase is expressed by the inhibition rate calculated by the following equation.

$$\text{Inhibition rate (\%)} = \frac{A - B}{A} \times 100$$

A: amount of $LTB_4$ formed in the absence of the test compound
B: amount of $LTB_4$ formed in the presence of the test compound Results As examples of the experimental results, Table 2 shows concentrations of compound Nos. 1-4 8, 1-9, 1-10, 1-11, 1-13, 1-16, 1-18, 1-23, 1-24, 1-25, 1-26, 1-28, 2-8, 2-9, 2-10, 2-11, 2-12, 2-13, 2-16, 2-25, 2-26, 2-30, 2-32, 2-33, 2-34, 2-35 and 2-39 required to inhibit $LTA_4$ hydrolase by 50%, i.e., $IC_{50}$.

TABLE 2

| | $IC_{50}$ (M) |
|---|---|
| Compound No. 1-8 | $1.2 \times 10^{-7}$ |
| Compound No. 1-9 | $1.7 \times 10^{-7}$ |
| Compound No. 1-10 | $1.2 \times 10^{-7}$ |
| Compound No. 1-11 | $3.2 \times 10^{-8}$ |
| Compound No. 1-13 | $1.0 \times 10^{-7}$ |
| Compound No. 1-16 | $1.1 \times 10^{-7}$ |
| Compound No. 1-18 | $1.0 \times 10^{-7}$ |
| Compound No. 1-23 | $3.0 \times 10^{-7}$ |
| Compound No. 1-24 | $3.1 \times 10^{-7}$ |
| Compound No. 1-25 | $5.1 \times 10^{-8}$ |
| Compound No. 1-26 | $2.0 \times 10^{-7}$ |
| Compound No. 1-28 | $2.9 \times 10^{-7}$ |
| Compound No. 2-8 | $2.8 \times 10^{-7}$ |
| Compound No. 2-9 | $7.2 \times 10^{-8}$ |
| Compound No. 2-10 | $2.0 \times 10^{-7}$ |
| Compound No. 2-11 | $2.4 \times 10^{-8}$ |
| Compound No. 2-12 | $5.8 \times 10^{-8}$ |
| Compound No. 2-13 | $1.4 \times 10^{-7}$ |
| Compound No. 2-16 | $4.6 \times 10^{-8}$ |
| Compound No. 2-25 | $1.5 \times 10^{-8}$ |
| Compound No. 2-26 | $1.6 \times 10^{-7}$ |
| Compound No. 2-30 | $5.5 \times 10^{-8}$ |
| Compound No. 2-32 | $2.5 \times 10^{-8}$ |
| Compound No. 2-33 | $6.7 \times 10^{-8}$ |
| Compound No. 2-34 | $6.8 \times 10^{-8}$ |
| Compound No. 2-35 | $7.9 \times 10^{-8}$ |
| Compound No. 2-39 | $5.5 \times 10^{-8}$ |

As shown in Table 2, the present compounds were found to inhibit the $LTA_4$ hydrolase activity remarkably at the low concentrations.

Comparison Test

The following comparison tests were carried out in order to show that it is an important requirement in order to exhibit the excellent activities that "Phenyl" is the phenyl group having the substituent and "Alkylene" is the ethylene group into which the lower alkyl group is introduced in the above-mentioned formula [II].

The following known compound [I] described in Chem. Pharm. Bull., 35, 2382–2387 (1987) was used as a compound of which "Phenyl" has no substituent, and the following known compound [II] described in Japanese Laid-open Patent Publication No. 39855/1988 was used as a compound of which "Alkylene" has a substituent other than the lower alkyl group.

Known compound [I]

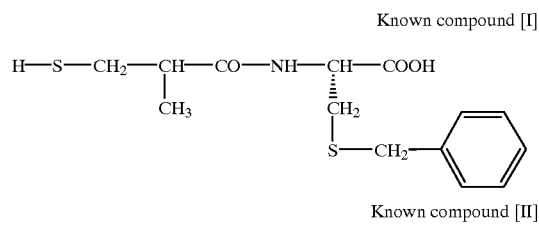

Known compound [II]

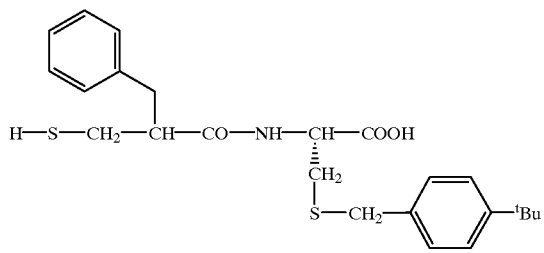

Experiments were carried out under the same conditions as those of the above-mentioned "Pharmacological Test".

As a result, the known compound [I] exhibited little inhibitory effect on $LTA_4$ hydrolase even at a concentration of $10^{-5}$ M.

In addition, $IC_{50}$ of the known compound [II] was $4.5 \times 10^{-6}$ M, and the compound [II] exhibited an inhibitory effect on $LTA_4$ hydrolase being only one tenth or less of those of the present compounds. In particular, the compound [II] exhibited the inhibitory effect on $LTA_4$ hydrolase being only about 1/100 of that of the present compound (No. 2-12), wherein the benzyl group is only replaced by a methyl group in the known compound [II].

The above-mentioned results clearly show that it is an important requirement in order to exhibit the excellent activities that "Phenyl" is the phenyl group having the substituent and "Alkylene" is the ethylene group into which the lower alkyl group is introduced in the formula [II].

Since the above-mentioned pharmacological test shows that the present compounds have the excellent inhibitory effects on $LTA_4$ hydrolase, the compounds are expected to be excellent medicines, in particular, therapeutic agents for inflammatory diseases such as rheumatic diseases, psoriasis, inflammatory intestinal diseases, gout and cystic fibrosis, in which $LTB_4$ is concerned.

Industrial Applicability

The present invention relates to novel sulfur-containing amino acid derivatives which have inhibitory effects on leukotriene $A_4$ hydrolase and are useful as medicines such as therapeutic agents for inflammatory diseases such as rheumatic diseases, psoriasis, inflammatory bowel diseases, gout and cystic fibrosis.

We claim:

1. A compound represented by the following formula (1) or a salt thereof,

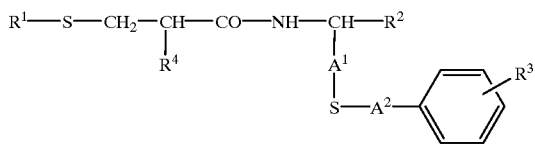

wherein
- $R^1$ represents a hydrogen atom, a lower alkyl group, a phenyl-lower alkyl group, a lower alkanoyl group or a benzoyl group, and each phenyl ring of the phenyl-lower alkyl group and the benzoyl group is unsubstituted or substituted by a lower alkyl group, a lower alkoxy group or a halogen atom;
- $R^2$ represents a carboxyl group or a carboxyl group which is converted into an ester, an amide or a hydroxamic acid;
- $R^3$ represents a hydroxyl group, a lower alkyl group, a lower cycloalkyl group, a halogeno-lower alkyl group, a lower alkoxy group, a halogeno-lower alkoxy group, a lower alkylthio group, a phenyl group, a phenoxy group, a phenylthio group, a halogen atom, a lower alkylsulfonyl group, a halogeno-lower alkylsulfonyl group, a nitro group or a cyano group, and each phenyl ring of the phenyl group, the phenoxy group and the phenylthio group is unsubstituted or substituted by a lower alkyl group or a lower alkoxy group;
- $R^4$ represents a lower alkyl group;
- A1 represents a lower alkylene group; and
- $A^2$ represents a lower alkylene group.

2. A compound represented by the following formula (1) or a salt thereof,

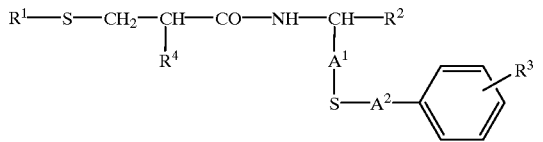

wherein
- $R^1$ represents a hydrogen atom, a lower alkanoyl group or a benzoyl group;
- $R^2$ represents a carboxyl group or a carboxyl group which is converted into a lower alkyl ester or a phenyl-lower alkyl ester; or a carboxyl group which is converted into an amine with a lower alkyl amine or a phenyl-lower alkyl amine;
- $R^3$ represents a lower alkyl group, a lower cycloalkyl group, a halogeno-lower alkyl group, a lower alkoxy group, a halogeno-lower alkoxy group, a lower alkylthio group, a phenyl group, a phenoxy group, a phenylthio group, a halogen atom, a lower alkylsulfonyl group, a halogeno-lower alkylsulfonyl group, a nitro group or a cyano group;
- $R^4$ represents a lower alkyl group;
- $A^1$ represents a lower alkylene group; and
- $A^2$ represents a lower alkylene group.

3. A compound represented by the following formula (1) or a salt thereof,

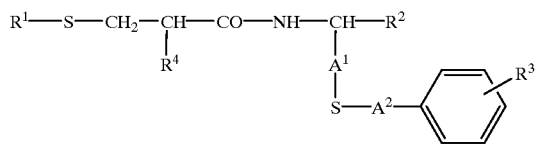

wherein
- $R^1$ represents a hydrogen atom, a lower alkanoyl group or a benzoyl group;
- $R^2$ represents a carboxylic acid or a carboxylic acid which is converted into a lower alkyl ester;
- $R^3$ represents a lower alkyl group, a lower cycloalkyl group, a halogeno-lower alkyl group, a lower alkoxy group, a halogeno-lower alkoxy group, a lower alkylthio group, a phenyl group, a phenoxy group, a halogen atom, a lower alkylsulfonyl group, a nitro group or a cyano group;
- $R^4$ represents a lower alkyl group;
- Al represents a lower alkylene group; and
- $A^2$ represents a lower alkylene group.

4. The compound or a salt thereof as claimed in claim 1, wherein
- $R^1$ represents a hydrogen atom, an acetyl group or a benzoyl group;
- $R^2$ represents a carboxyl group, a methoxycarbonyl group or an ethoxycarbonyl group;
- $R^3$ represents a methyl group, an ethyl group, a propyl group, an isopropyl group, a tert-butyl group, a trifluoromethyl group, a methoxy group, a ethoxy group, a cyclohexyl group, a trifluoromethoxy group, a methylthio group, a phenyl group, a phenoxy group, a fluorine atom, a chlorine atom, a bromine atom, an iodine atom, a methylsulfonyl group, a nitro group or a cyano group;
- $R^4$ represents a methyl group;
- $A^1$ represents a methylene group, a methylmethylene group or a dimethylmethylene group; and
- $A^2$ represents a methylene group, a methylmethylene group, a dimethylmethylene group, an ethylmethylene group, a propylmethylene group, an isopropylmethylene group or a butylmethylene group.

5. A compound represented by the following formula [I] or a salt thereof,

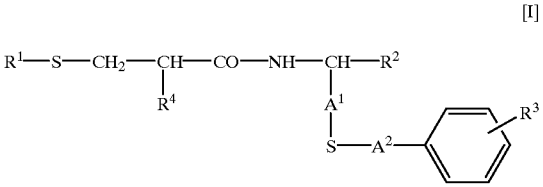

wherein
- $R^1$ represents a hydrogen atom or a benzoyl group;
- $R^2$ represents a carboxyl group;
- $R^3$ represents a lower alkyl group, a lower cycloalkyl group, a halogeno-lower alkyl group, a lower alkylthio group or a halogen atom;
- $R^4$ represents a lower alkyl group;

$A^1$ represents a lower alkylene group; and $A^2$ represents a lower alkylene group.

6. The compound or a salt thereof as claimed in claim 1, wherein $R^3$ represents an isopropyl group, a tert-butyl group, a cyclohexyl group, a trifluoromethyl group, a methylthio group or an iodine atom;

$R^4$ represents a methyl group;

$A^1$ represents a methylene group or a dimethylmethylene group; and $A^2$ represents methylene group, a methylmethylene group, a dimethylmethylene group or an ethylmethylene group.

7. A compound selected from the group consisting of (2R)-2-[(2S)-3-(benzoylthio)-2-methylpropionylamino]-3-(4-isopropylbenzylthio)propionic acid, (2R)-2-[(2S)-3-(benzoylthio)-2-methylpropionylamino]-3-(4-tert-butylbenzylthio)propionic acid, (2R)-2-[(2S)-3-(benzoylthio)-2-methylpropionylamino]-3-(4-methylthiobenzylthio)propionic acid, (2R)-2-[(2S)-3-(benzoylthio)-2-methylpropionylamino]-3-(4-iodobenzylthio)propionic acid, (2R)-3-(4-isopropylbenzylthio)-2-[(2S)-3-mercapto-2-methylpropionylamino]propionic acid, (2R)-3-(4-tert-butylbenzylthio)-2-[(2S)-3-mercapto-2-methylpropionylamino]propionic acid, (2R)-3-(4-tert-butylbenzylthio)-2-[(2RS)-3-mercapto-2-methylpropionylamino]propionic acid, (2R)-2-[(2S)-3-mercapto-2-methylpropionylamino]-3-(4-methylthiobenzylthio)propionic acid, (2R)-3-(4-iodobenzylthio)-2-[(2S)-3-mercapto-2-methylpropionylamino]propionic acid, (2R)-2-[(2S)-3-mercapto-2-methylpropionylamino]-3-[(α-methyl-4-isopropyl) benzylthio]propionic acid, (2R)-2-[(2S)-3-mercapto-2-methylpropionylamino]-3-[(α,α-dimethyl-4-isopropyl)benzylthio]propionic acid, (2R)-3-[(α-ethyl-4-isopropyl)benzylthio]-2-[(2S)-3-mercapto-2-methylpropionylamino]propionic acid, (2R)-3-[(4-tert-butyl-α-methyl)benzylthio]-2-[(2R)-3-mercapto-2-methylpropionylamino]propionic acid, (2R)-3-(4-cyclohexyl benzylthio)-2-[(2S)-3-mercapto-2-methylpropionylamino]propionic acid, (2R)-3-[(4-cyclohexyl-α,α-dimethyl)benzylthio]-2-[(2S)-3-mercapto-2-methylpropionylamino]propionic acid and salts thereof.

8. A pharmaceutical composition comprising a compound or a salt thereof as claimed in claim 1 together with a pharmaceutical carrier.

9. A pharmaceutical composition comprising a compound or a salt thereof as claimed in claim 2 together with a pharmaceutical carrier.

10. A pharmaceutical composition comprising a compound or a salt thereof as claimed in claim 3 together with a pharmaceutical carrier.

11. A pharmaceutical composition comprising a compound or a salt thereof as claimed in claim 4 together with a pharmaceutical carrier.

12. A pharmaceutical composition comprising a compound or a salt thereof as claimed in claim 5 together with a pharmaceutical carrier.

13. A pharmaceutical composition comprising a compound or a salt thereof as claimed in claim 6 together with a pharmaceutical carrier.

14. A pharmaceutical composition comprising a compound or a salt thereof as claimed in claim 7 together with a pharmaceutical carrier.

15. The compound or a pharmaceutically acceptable salt thereof as claimed in claim 1, wherein $R^1$ is a hydrogen atom; a $C_1$–$C_6$ alkyl group; a phenyl-$C_1$–$C_6$ alkyl group, wherein the phenyl group thereof is unsubstituted or substituted by a $C_1$–$C_6$ alkyl group, a $C_1$–$C_6$ alkoxy group, fluorine, chlorine, bromine or iodine; a $C_2$–$C_6$ alkanoyl group or a benzoyl group which is unsubstituted or substituted by a $C_1$–$C_6$ alkyl group, a $C_1$–$C_6$ alkoxy group; or a halogen atom selected from the group consisting of fluorine, chlorine, bromine and iodine;

$R^3$ is a hydroxyl group; a $C_1$–$C_6$ alkyl group; a $C_3$–$C_8$ cycloalkyl group; a halogeno-$C_1$–$C_6$ alkyl group; a $C_1$–$C_6$ alkoxy group; a halogeno-$C_1$–$C_6$ alkoxy group; a $C_1$–$C_6$ alkylthio group, a phenyl ring which is unsubstituted or substituted by a $C_1$–$C_6$ alkyl group or a $C_1$–$C_6$ alkoxy group; a phenoxy group which is unsubstituted or substituted by a $C_1$–$C_6$ alkyl group or a $C_1$–$C_6$ alkoxy group; a phenylthio group, wherein the phenyl group thereof is unsubstituted or substituted by a $C_1$–$C_6$ alkyl group or a $C_1$–$C_6$ alkoxy group; a halogen selected from the group consisting of fluorine, chlorine, bromine and iodine; a $C_1$–$C_6$ alkylsulfonyl group; a halogeno-$C_1$–$C_6$ alkylsulfonyl group; a nitro group or a cyano group;

$R^4$ is a $C_1$–$C_6$ alkyl group;

$A^1$ is a $C_1$–$C_6$ alkylene group; and $A^2$ is a $C_1$–$C_6$ alkylene group.

16. The compound or pharmaceutically acceptable salt thereof as claimed in claim 2, wherein $R^1$ is a hydrogen atom, a $C_2$–$C_6$ alkanoyl group or a benzoyl group;

$R^2$ is a carboxyl group, a carboxyl group which is converted into a $C_1$–$C_6$ ester or a phenyl-$C_1$–$C_6$ alkyl ester, a carboxyl group which is converted into an amide with a $C_1$–$C_6$ alkyl amine or a phenyl-$C_1$–$C_6$ alkyl amine;

$R^3$ is a $C_1$–$C_6$ alkyl group; a $C_3$–$C_8$ cycloalkyl group; a halogeno-$C_1$–$C_6$ alkyl group; a $C_1$–$C_6$ alkoxy group; a halogeno-$C_1$–$C_6$ alkoxy group; a $C_1$–$C_6$ alkylthio group; a phenyl group; a phenoxy group; a phenylthio group; a halogen atom selected from the group consisting of fluorine, chlorine, bromine and iodine; a $C_1$–$C_6$ alkylsulfonyl group, a nitro group or a cyano group;

$R^4$ is a $C_1$–$C_6$ alkyl group;

$A^1$ is a $C_1$–$C_6$ alkylene group; and $A^2$ is a $C_1$–$C_6$ alkylene group.

17. The compound or pharmaceutically acceptable salt thereof as claimed in claim 3, wherein $R^1$ is a hydrogen atom, a $C_2$–$C_6$ alkanoyl group or a benzoyl group;

$R^2$ is a carboxylic acid or a carboxylic acid which is converted into a $C_1$–$C_6$ alkyl ester;

$R^3$ is a $C_1$–$C_6$ alkyl group; a $C_3$–$C_8$ cycloalkyl group; a halogeno-$C_1$–$C_6$ alkyl group; a $C_1$–C6 alkoxy group; a halogeno-$C_1$–$C_6$ alkoxy group; a $C_1$–$C_6$ alkylthio group; a phenyl group; a phenoxy group; a halogen atom selected from the group consisting of fluorine, chlorine, bromine and iodine; a $C_1$–$C_6$ alkylsulfonyl group; a nitro group or a cyano group;

$R^4$ is a $C_1$–$C_6$ alkyl group;

$A^1$ is a $C_1$–$C_6$ alkylene group; and $A^2$ is a $C_1$–$C_6$ alkylene group.

18. The compound or a pharmaceutically acceptable salt thereof as claimed in claim 5, wherein $R^3$ is a $C_1$–$C_6$ alkyl group, a $C_3$–$C_8$ cycloalkyl group, a halogeno-$C_1$–$C_6$ alkyl group, a $C_1$–$C_6$ alkylthio group or a halogen atom selected from the group consisting of fluorine, chlorine, bromine and iodine;

$R^4$ is a $C_1$–$C_6$ alkyl group;

$A^1$ is a $C_1$–$C_6$ alkylene group; and $A^2$ is a $C_1$–$C_6$ alkylene group.

* * * * *